United States Patent
Soliman et al.

(10) Patent No.: US 7,984,712 B2
(45) Date of Patent: Jul. 26, 2011

(54) PATIENT CIRCUIT DISCONNECT SYSTEM FOR A VENTILATOR AND METHOD OF DETECTING PATIENT CIRCUIT DISCONNECT

(75) Inventors: Ihab S. Soliman, Laguna Niguel, CA (US); Vern Brightup, Placentia, CA (US)

(73) Assignee: Bird Products Corporation, San Diego, CA (US)

( * ) Notice: Subject to any disclaimer, the term of this patent is extended or adjusted under 35 U.S.C. 154(b) by 1359 days.

(21) Appl. No.: 10/972,851

(22) Filed: Oct. 25, 2004

(65) Prior Publication Data
US 2006/0086357 A1    Apr. 27, 2006

(51) Int. Cl.
 A61M 16/00    (2006.01)
 A62B 9/00     (2006.01)
 A62B 27/00    (2006.01)
 G08B 3/00     (2006.01)
 G08B 5/00     (2006.01)

(52) U.S. Cl. ......... 128/202.22; 128/204.21; 128/204.22; 128/204.18

(58) Field of Classification Search ............. 128/204.22, 128/204.18, 204.26, 204.29, 204.21, 204.23, 128/200.24, 202.22; 600/529, 533, 538
See application file for complete search history.

(56) References Cited

U.S. PATENT DOCUMENTS

| | | | | |
|---|---|---|---|---|
| 3,595,228 A * | 7/1971 | Simon et al. | ............. | 128/202.22 |
| 4,031,885 A * | 6/1977 | Davis et al. | .................... | 600/533 |
| 4,155,357 A * | 5/1979 | Dahl | ........................ | 128/202.22 |
| 4,316,182 A * | 2/1982 | Hodgson | ....................... | 340/606 |
| 4,351,344 A * | 9/1982 | Stenzler | ......................... | 600/533 |
| 4,550,726 A * | 11/1985 | McEwen | .................. | 128/202.22 |
| 5,640,149 A * | 6/1997 | Campbell | ..................... | 340/626 |
| 5,782,233 A * | 7/1998 | Niemi et al. | ............. | 128/202.22 |
| 5,794,614 A * | 8/1998 | Gruenke et al. | ......... | 128/204.21 |
| 5,881,717 A | 3/1999 | Isaza | | |
| 5,915,381 A * | 6/1999 | Nord | ......................... | 128/204.23 |
| 5,984,872 A * | 11/1999 | Vriend | .......................... | 600/529 |
| 6,279,569 B1 * | 8/2001 | Berthon-Jones | ......... | 128/200.24 |
| 6,536,432 B2 * | 3/2003 | Truschel | .................. | 128/205.23 |
| 6,874,502 B1 * | 4/2005 | Nashed | ..................... | 128/205.23 |
| 2005/0051167 A1 * | 3/2005 | Biondi et al. | ............ | 128/204.21 |

* cited by examiner

*Primary Examiner* — Justine R Yu
*Assistant Examiner* — Colin Stuart

(57) ABSTRACT

A method of detecting disconnect of a patient circuit of a ventilation system, wherein a circuit disconnect is detected with a first sensitivity and a second sensitivity. The circuit disconnect detected with the first sensitivity is performed by detecting a volume loss for a minimum period of time, detecting a peak pressure loss for at least two consecutive breathing cycles or a minimum period of time, and detecting a pressure loss continuing for a predetermined period of time. The circuit disconnect detected with the second sensitivity is performed by detecting a volume loss for a single breathing cycle, detecting a pressure loss for a single breathing cycle, and detecting an increase of compliance. The first sensitivity is lower than the second sensitivity. Preferably, an alarm is activated when the circuit disconnect is detected with the first sensitivity, and subsystems of the ventilation system is informed of the circuit disconnect that has been detected with the second sensitivity.

44 Claims, 16 Drawing Sheets

PATENT CIRCUIT DISCONNECT SYSTEM FOR A VENTILATOR AND METHOD OF DETECTING PATIENT CIRCUIT DISCONNECT

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

The present invention relates in general to a method and a system for detecting a patient circuit disconnect of a ventilation system, and more particularly, to a method that not only detects patient circuit disconnect occurring in various locations of the circuit, but also informs critical subsystems of the ventilation system of the disconnect and/or a possible disconnect of the patient circuit.

When a patient's respiratory system cannot provide adequate oxygenation and/or ventilation, a mechanical ventilation system is typically used to provide breathing gas, particularly, supplemental oxygen to a patient through a patient circuit. The patient circuit generally has an inspiratory line and an expiratory line connected to an inspiratory port and an expiratory port of a wye fitting. The wye fitting further has a patient port connected to a patient. The mechanical ventilation is either supplied by intubating the patient by an endotracheal tube connected to the patient port of the wye fitting or by providing the patient with a face mask or a hood. The inspiratory line is also connected to a pneumatic system of ventilator from which the breathing gas is supplied, and the expiratory line conveys the gas exhaled by the patient to the ventilator and/or ambient air.

Disconnects of the patient circuit can typically occur in various areas of the patient circuit, including disconnect within the inspiratory line, disconnect within the expiratory line, and disconnect at the patient port of the wye fitting. When the patient is intubated with the endotracheal tube, disconnect may also occur at the patient upon endotracheal tube extabation. The disconnect at any of the above areas normally results in insufficient breathing gas being provided from the ventilator to the patient, which may consequently cause impairment or possible collapse of the lung of the patient.

Prior art systems and methods for detecting disconnect of a patient circuit have been developed which typically generate an alarm indicating the disconnect occurring in the patient circuit so as to prevent lung collapse due to circuit disconnect. However, the reliability of such conventional systems and methods is often affected by the location of the disconnect, the ventilation mode being used, the tubing size and length selection, and the physical size of the patient.

Therefore a substantial need exists in the art to provide a method and/or a device which detects circuit disconnects in a reliable and timely manner for a ventilation system regardless of disconnect locations, ventilation mode, patient size, and/or patient breathing pattern.

BRIEF SUMMARY OF THE INVENTION

The present invention addresses and alleviates the above referenced deficiencies associated in the art by providing an apparatus and a method of detecting disconnect of a patient circuit of a ventilation system in a reliable and timely manner, wherein the circuit disconnect is preferably detected by a first detection algorithms and a second detection algorithm. The first detection algorithm provides a primary output for the main alarm of the ventilation system. The second detection algorithm provides a secondary output for a more reactive indication of a disconnect or a potential disconnect to inform other onboard subsystems (typically closed-loop subsystems) of the ventilation system whose feedback signals can be severely affected by the disconnect of a circuit disconnect. For example, the exhalation valve servo controlling positive end expiratory pressure (PEEP) must be informed by the start of the expiratory phase of a circuit disconnect which may have caused a PEEP error during previous breath. This will prevent the adaptive system from inappropriately compensating for the pressure loss due to disconnect or potential disconnect.

As the first detection algorithm provides the primary output for the main alarm, to avoid activating the main alarm by disconnect condition caused by noise or short-term fluctuation, the first detection algorithm is less sensitive than the second detection algorithm. That is, the first detection algorithm requires the disconnect condition to be detected for at least one predetermined period of time or two consecutive breaths, while the second detection algorithm basically requires detection of only one single breath.

The first detection algorithm includes three sub-algorithms for detecting long-term volume loss, consecutive-breath pressure loss, and continuous pressure loss. In the sub-algorithm for detecting long-term volume loss, a volume loss is determined based on the percentage of volume leakage, which reflects the volume difference between the inspiratory gas and expiratory gas. When the volume leakage exceeds a predetermined percentage for the first predetermined period of time, a long-term volume loss is detected. In the sub-algorithm for detecting consecutive-breath pressure loss, a threshold pressure is calculated based on the baseline pressure setting. When a selected pressure reading is less than the threshold pressure during a breath longer than a second predetermined period of time, or when the selected pressure reading is less than the threshold pressure for two consecutive breaths, a pressure loss is detected. In the continuous pressure loss detection sub-algorithm, a threshold pressure is determined in the similar manner used in the consecutive-breath pressure loss sub-algorithm. When a selected pressure reading is lower than the threshold pressure for a third predetermined period of time, the continuous pressure loss is detected. However, instead of selecting the peak expiratory gas pressure, the expiratory gas pressure that may change anytime when a disconnect occurs is used to compare with the threshold pressure, so as to determine whether a continuous pressure loss is detected.

The second detection algorithm also includes three sub-algorithms for detecting a short-term volume loss, a single-breath pressure loss and a compliance change. In the sub-algorithm for detecting a short-term volume loss, the percentage of volume leakage for a single breath is compared to the predetermined percentage as defined in the long-term volume loss detection. When the percentage of volume leakage exceeds the predetermined percentage, the short-term volume loss is detected. The short-term volume loss can thus be referred as a single-breath volume loss. The sub-algorithm for detecting single-breath pressure loss is basically the same as the sub-algorithm for detecting consecutive-breath pressure loss apart from that the pressure loss is detected without the requirement of a breath longer than the second predetermined period of time or two consecutive breaths.

The sub-algorithm for detecting the compliance change basically declares a disconnect when the compliance increase reaches a certain range. Preferably, the compliance increase is calculated based on the volume of inspiratory gas and the pressure change between the expiratory pressure in an inspiratory phase and the positive end expiratory pressure.

The present invention also provides a ventilation system comprising an inspiratory flow sensor, an expiratory flow sensor, an expiratory pressure sensor, a first set of processing units and a second set of processing units. The inspiratory flow sensor is operative to measure an inspiratory flow of a patient circuit of the ventilation system, the expiratory flow sensor is operative to measure an expiratory flow of the patient circuit, and the pressure sensor is operative to measure an expiratory pressure of the patient circuit. The first set of processing units is operative to perform the first detection algorithm, and the second set of processing units is operative to perform the second detection algorithm. Thereby, the main alarm can be triggered in a more reliably and time manner, while the on-board sub-systems can be properly adjusted when a short-term disconnect occurs.

BRIEF DESCRIPTION OF THE DRAWINGS

These as well as other features of the present invention will become more apparent upon reference to the drawings wherein.

DETAILED DESCRIPTION OF THE INVENTION

Figure 1:
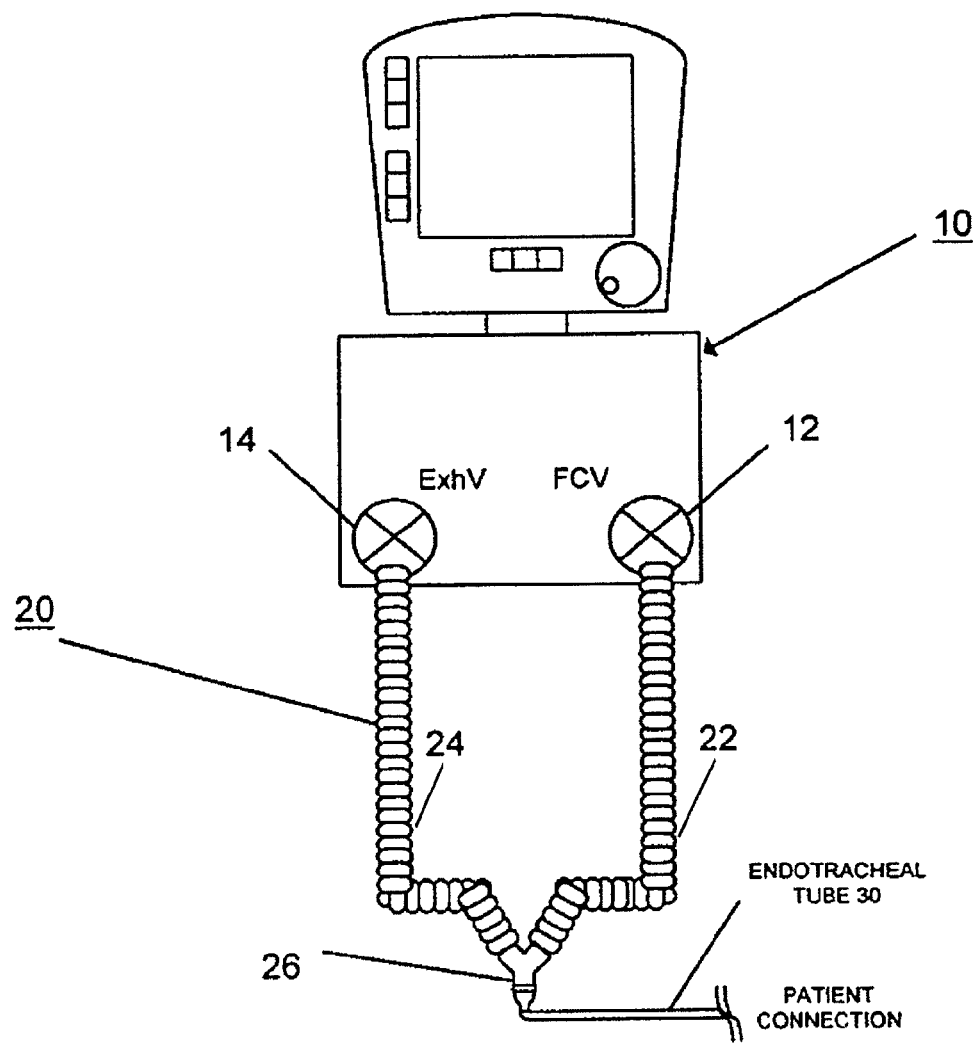
FIG. 1 shows a ventilator system.

Referring now to the drawings wherein the showings are for purpose of illustrating preferred embodiments of the present invention only, and not for purposes of limiting the same, FIG. 1 shows a ventilation system which comprises a ventilator 10 and a patient circuit 20. The ventilator 10 has an inspiratory port 12 from which breathing gas is supplied to the patient circuit 20 and an expiratory port 14 for receiving gas exhaled from the patient through the patient circuit 20. The patient circuit 20 has an inspiratory line 22 connected to the inspiratory port 12 and an expiratory line 24 connected to the expiratory port 14. Both of the inspiratory line 22 and the expiratory line 24 are connected to a wye-fitting 26, which establishes the connection between the inspiratory and expiratory lines 22 and 24 to the patient via an endotracheal tube, mask or hood 30. Typically, the ventilator 10 has a pneumatic system for providing the breathing gas and an expiratory gas processing unit processing the gas exhaled by the patient.

Figure 2:
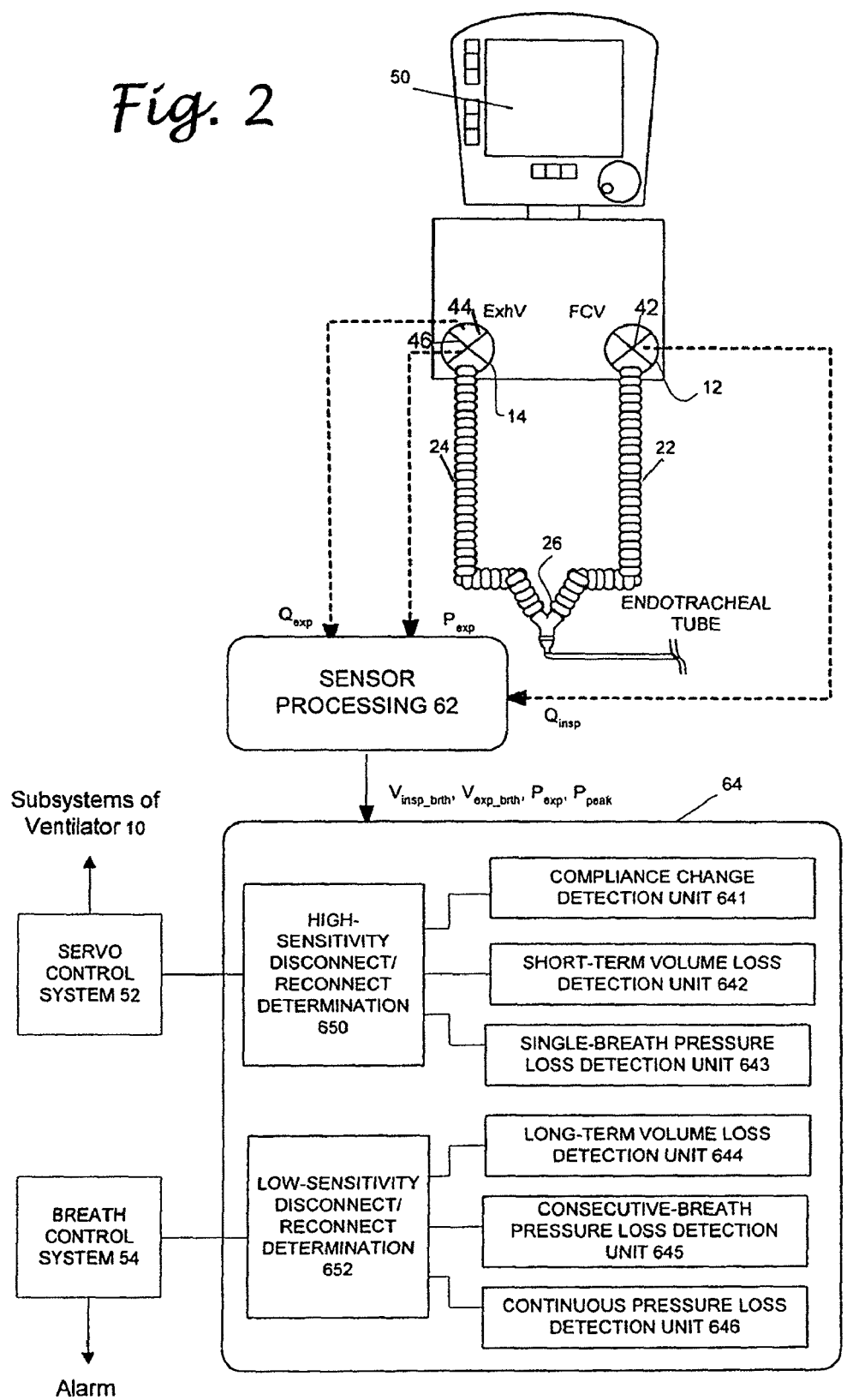
FIG. 2 is a block diagram of a ventilation system having the circuit disconnect detection and warning system of the present invention.

As shown in FIG. 2, a flow sensor 42 is installed in the inspiratory line 22 or the inspiratory port 12 for monitoring the flow rate of the breathing gas $Q_{insp}$; a flow sensor 44 is installed in the expiratory line 24 or the expiratory port 14 for monitoring the flow rate $Q_{exp}$ of the gas exhaled by the patient; and a pressure sensor 46 is installed at the expiratory port 14 or the expiratory line 24 for measuring the gas pressure $P_{exp}$ in the expiratory line 24. Other flow and pressure sensors may also be installed in various locations of the patient circuit 20. For example, pressure sensors may also be installed in the inspiratory port 12 or line 22 and/or the Wye fitting 26. In the preferred embodiment, the output readings of the flow sensors 42 and 44 and the pressure sensor 46 are input to a signal processing unit 62. The signal processing unit 62 integrates the flow rates $Q_{insp}$ and $Q_{exp}$ into inspiratory and expiratory volumes $V_{insp}$ and $V_{exp}$ and captures both the real time expiratory pressure $P_{exp}$ and the peak expiratory pressure $P_{peak}$ for every breathing cycle as parameters for detecting disconnects occurring in various locations of the patient circuit 20.

The ventilation system of the present invention preferably comprises a processor 64, in which a set of high-sensitivity detection units for performing a high-sensitivity detection algorithm and a set of low-sensitivity detection units for performing a low-sensitivity detection algorithm are installed. The high-sensitivity detection units include a compliance change detection unit 641, a short-term volume loss detection unit 642, and a single-breath pressure loss detection unit 643. The low-sensitivity detection units include a long-term volume loss detection unit 644, a consecutive-breath volume loss detection unit 645, and a continuous pressure loss detection unit 646. The detection outputs of the compliance change detection unit 641, the short-term volume loss detection unit 642 and the single-breath pressure loss detection unit 643 are input into a high-sensitivity disconnect determination unit 650. The high-sensitivity disconnect determination unit 650 provides an output signal to inform other on-board system such as a servo control system 52 of subsystems of the ventilator 10 of the disconnect condition of the patient circuit 20. The detection outputs of the long-term volume loss detection unit 644, the consecutive-breath pressure loss detection unit 645 and the continuous pressure loss detection unit 646 are input into a low-sensitivity disconnect determination unit 652, which then provides an output signal to a breath control system 54. When the signal indicates a disconnect in the patient circuit 20, the breath control system 54 is operative to generate an alarm such as an audio or visual warning signal.

Figure 3:
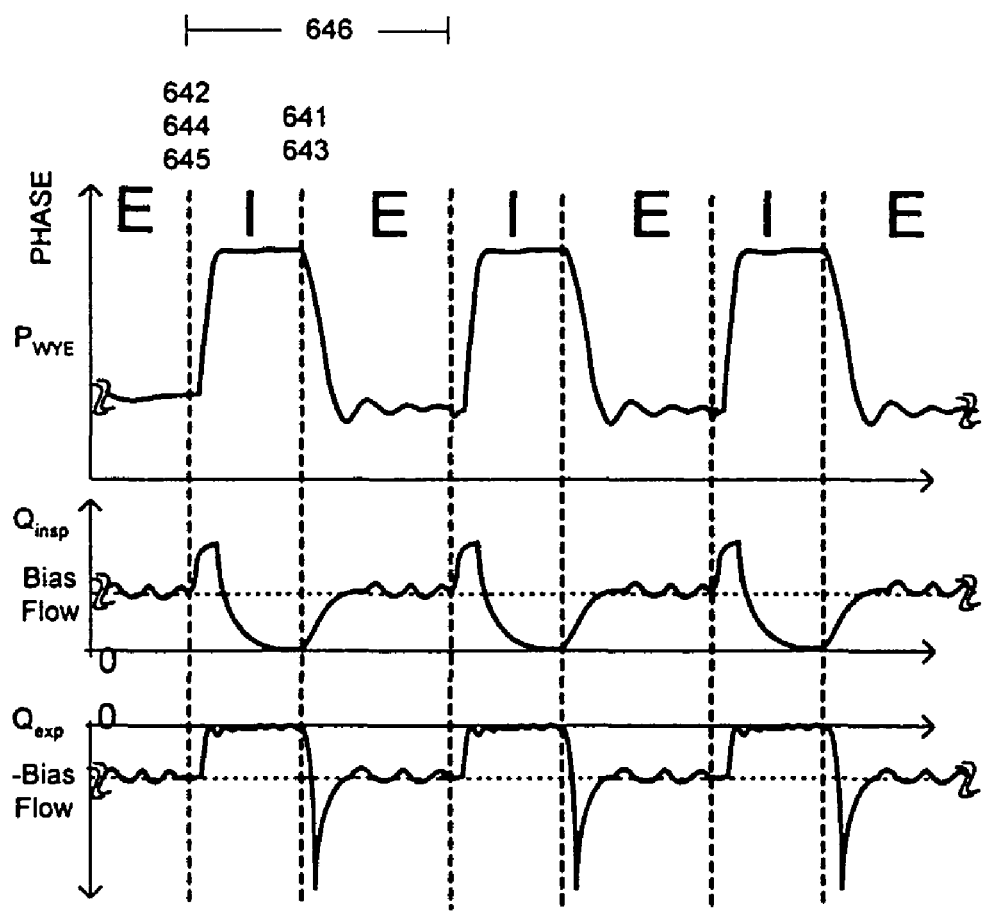
FIG. 3 shows the pressure, inspiratory gas flow and the expiratory gas flow for a normal breath under pressure controlled mode.

The ventilation system preferably includes a monitor 50 for displaying the settings of the ventilator 10, the breathing condition of the patient, and/or the condition of the gas supplied by the pneumatic system of the ventilator. FIG. 3 shows the pressure at the Wye fitting 26, the inspiratory flow rate $Q_{insp}$ and the expiratory flow rate $Q_{exp}$ for normal breaths of a patient under a pressure-control mode. As shown, in normal breaths, the pressure at the Wye fitting 26 increases up to a peak pressure value $P_{peak}$ from the beginning of each inspiratory phase I, and starts to fall to a low pressure value from the beginning of each expiratory phase E. The pressure at the Wye fitting 26 stays at the low pressure value until the beginning of the next inspiratory phase I. The inspiratory gas flow $Q_{insp}$ rises sharply to a peak value at the beginning of each inspiratory phase, and falls quickly to zero within the same inspiratory phase I. At the beginning of the following expiratory phase, the inspiratory gas flow $Q_{insp}$ starts to rise from zero to a peak bias flow until the beginning of the next inspiratory phase I. The expiratory gas flows $Q_{exp}$ is a negative bias flow with respect to the inspiratory gas flow $Q_{insp}$. At the beginning of each inspiratory phase I, the expiratory gas flow $Q_{exp}$ rises from a negative flow rate to zero. Such zero flow rate continues for the remaining inspiratory phase I. At the beginning of the following expiratory phase E, the flow rate drops sharply to a trough value and immediately reflects back to the previous negative flow rate as the patient exhales.

The low-sensitivity detection algorithm is performed to generate an output for activating the main circuit-disconnect alarm, such that a timely and reliable detection of the circuit disconnected can be obtained, while a false alarm caused by noise or fluctuation within a short term is avoided. The high-sensitivity detection program is performed to generate an output to inform devices of various subsystems of the ventilation system which are typically equipped with self-learning functions or software to adjust the operation parameters in accordance with variation of breathing conditions. For example, when an expiratory pressure loss is detected, an on-board adaptive system may add pressure for maintaining the positive end expiratory pressure (PEEP). This consequently increases the PEEP value when the patient circuit 20 is reconnected. Therefore, it is desirable that the adaptive system be informed of the circuit disconnect with a high sensitivity to avoid the false or incorrect learning and/or inappropriate self adjustment.

The high-sensitivity detection algorithm is also considered critical to control of patient flow delivery or gas pressure within the patient circuit which is limited or even stopped when feedback signals such as those representing gas pressure and flow in the patient circuit are disturbed or even unavailable due to circuit disconnect. Therefore, the circuit disconnect algorithm generates a disconnect alarm with a first, low sensitivity when a circuit disconnect is detected, but also preferably generates a signal to inform subsystems of the ventilation system of disconnect or potential disconnect of the patient circuit with a second, high detection sensitivity. The low-sensitivity detection of patient circuit disconnect is normally obtained when a pressure loss or volume loss occurs for a relatively long period of time compared to the high-sensitivity detection. The relatively long period of time depends on many factors including the settings of the ventilation system and physical conditions, including the size, weight, and health condition of the patient. In contrast, the high-sensitivity detection of patient circuit disconnect is normally obtained when the pressure or volume loss occurs for a single breath regardless how much time such disconnect has occurred. Thereby, the user or the therapist can reconnect the circuit to prevent lung collapse while preventing false learning or improper operations of on-board subsystems of the ventilation system.

Figure 4:
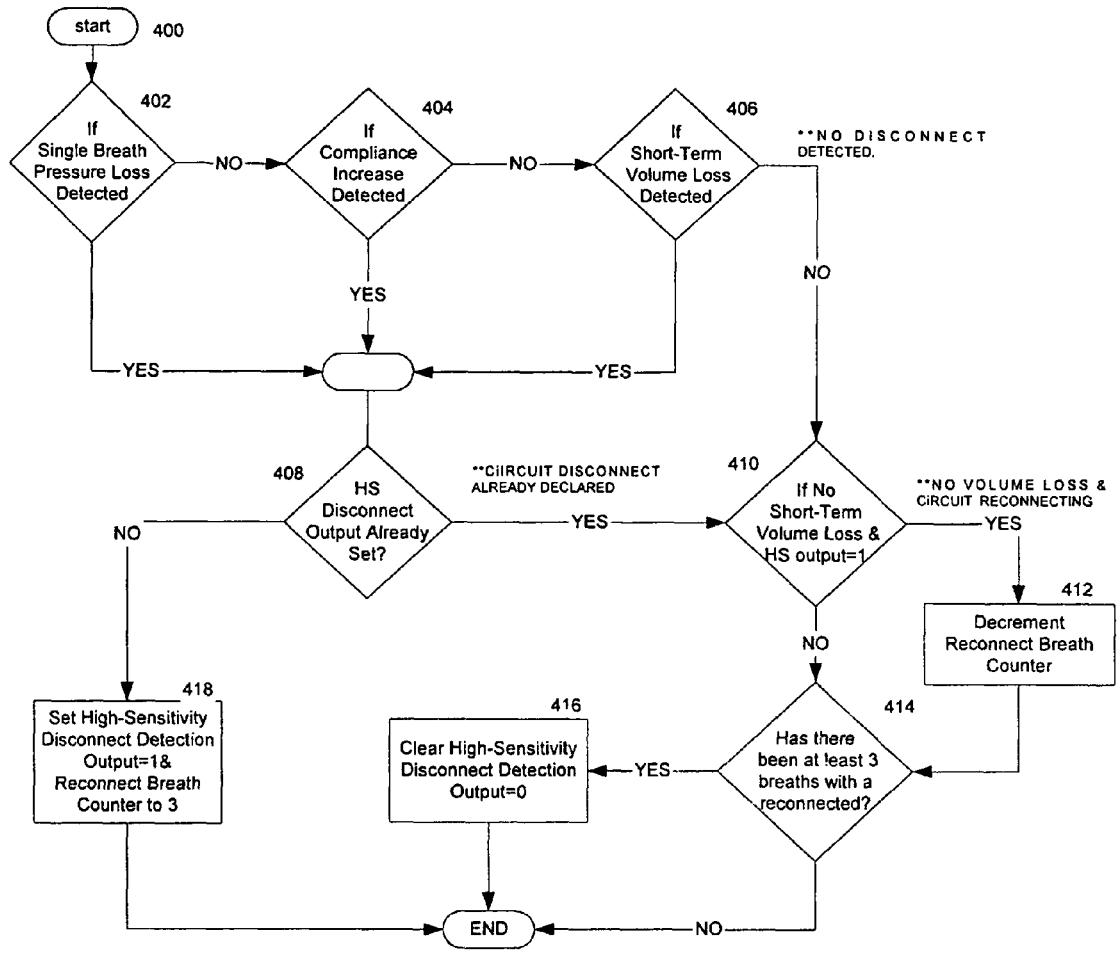
FIG. 4 is a flow chart showing a high-sensitivity disconnect detection algorithm of a patient circuit.
Figure 5:
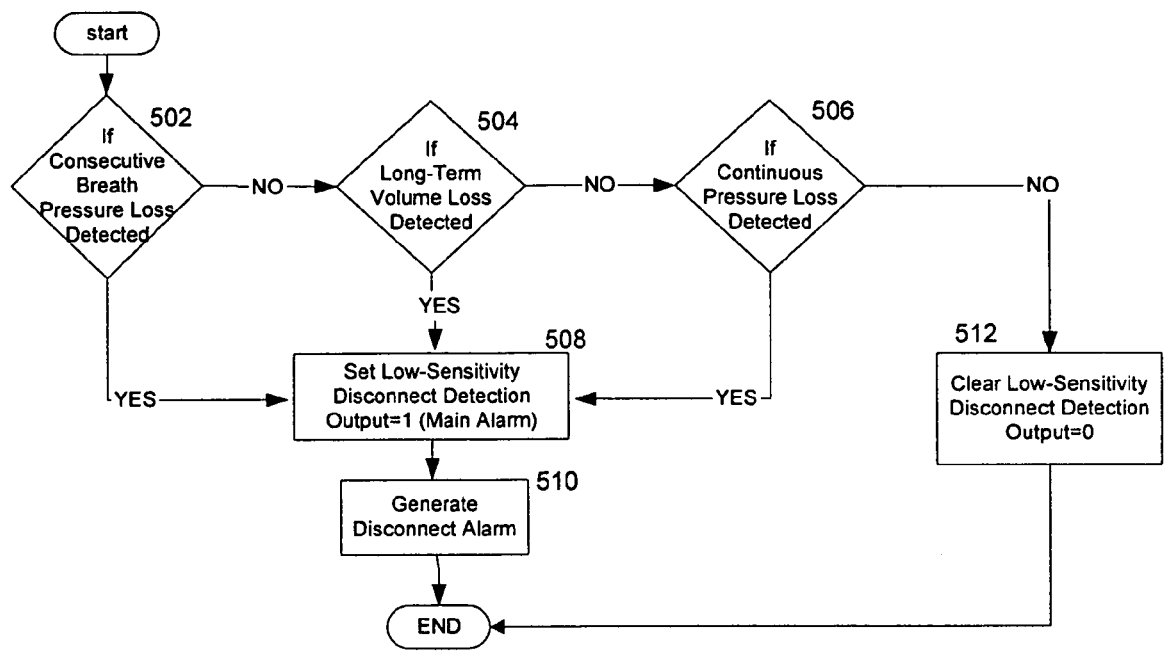
FIG. 5 is a flow chart showing a low-sensitivity disconnect detection algorithm of a patient circuit.
Figure 6:
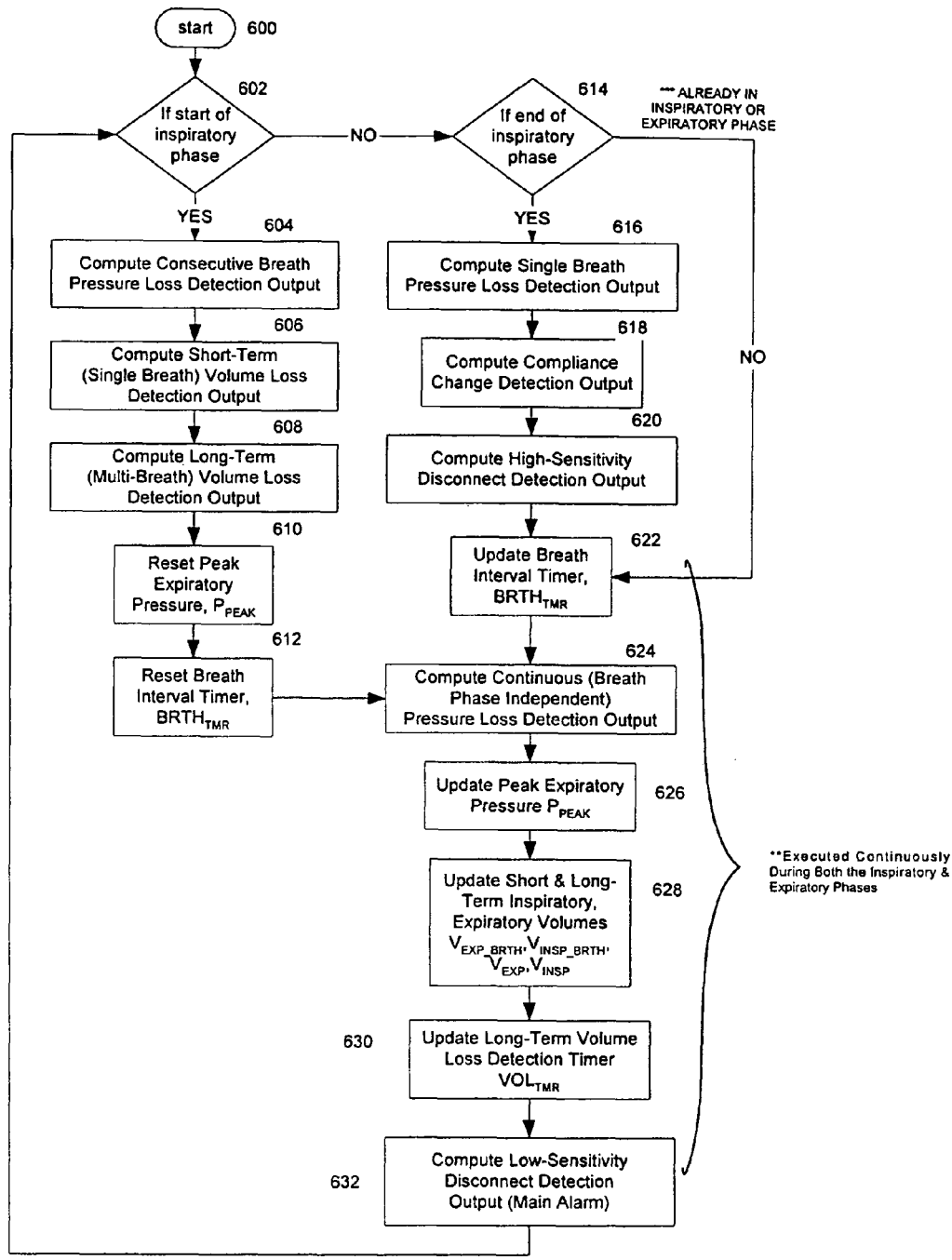
FIG. 6 is a flow chart showing a complete circuit disconnect detection algorithm that includes both the low- and high-sensitivity disconnect detection algorithms as shown in FIGS. 4,5.
Figure 7:
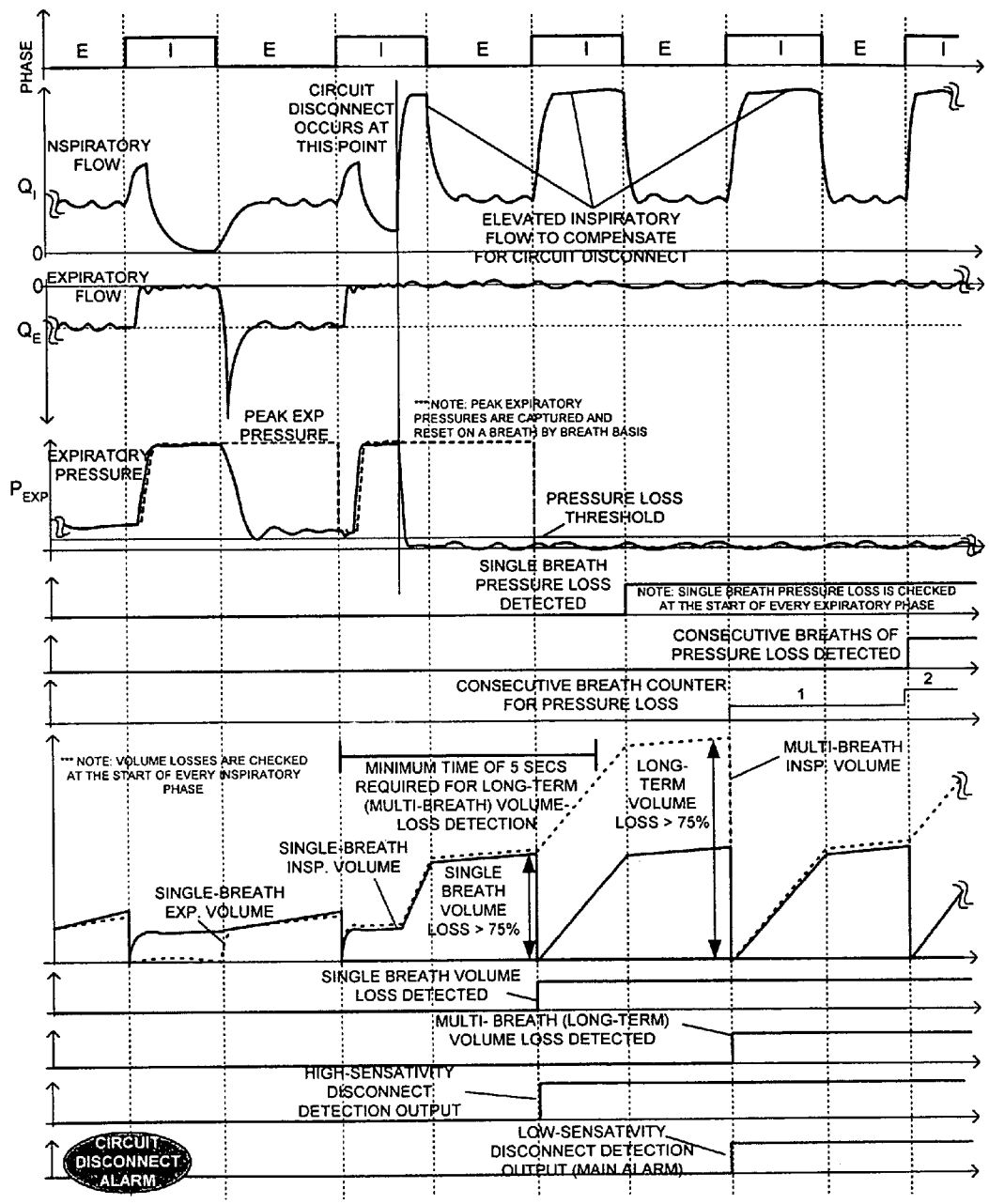
FIG. 7 shows the response of the inspiratory and expiratory gas flow, the expiratory pressure and the inspiratory and expiratory gas volume when a circuit disconnect occurs.

FIGS. 4 and 5 show the high- and low-sensitivity detection algorithms, respectively, FIG. 6 shows the complete algorithm including both the high- and low-sensitivity detection algorithms as shown in FIGS. 4 and 5. FIG. 7 illustrates the response of inspiratory gas flow $Q_{insp}$, expiratory gas flow $Q_{exp}$, expiratory gas pressure $P_{exp}$, inspiratory gas volume $V_{insp\_brth}$ for a single breath, expiratory gas volume $V_{exp\_brth}$ for the single breath, accumulated inspiratory and expiratory gas volumes $V_{insp}$ and $V_{exp}$ when a disconnect occurs in the ventilation system 10.

As shown in FIG. 4, when any of single-breath pressure loss, compliance increase and short-term volume loss is detected in steps 402, 404 or 406, whether a disconnect output has been set is determined in step 408. If the disconnect output has not been set, the high-sensitivity disconnect detection output is set as logic "1", and a counter for counting breaths upon reconnection is set to 3 breaths in step 418. If no disconnect has been detected in steps 402, 404 and 406, or when disconnect has been detected in any of the steps 402, 404, 406 and the detection output has been set at "1" in step 408 already, whether there is a short-term volume loss is determined in step 410. If no volume loss has been detected and the high-sensitivity detection output has been set at "1", the reconnect breath counter is decremented in step 412. If a volume loss has been detected in step 410, or after the reconnect breath counter has been decremented in step 412, the number of breaths taken by the patient after a circuit reconnect is counted in step 414. If there has been at least 3 breaths after the circuit reconnect is performed, the high-sensitivity disconnect detection output is cleared as "0" in step 416. After the breath counter is set to 3 breaths in step 418, or the high-sensitivity disconnect detection output is set at "0" in step 416, or when there is less than 3 breaths upon circuit reconnection after the high-sensitivity disconnect detection is set as "1" in step 414, a timer $BRTH_{TMR}$ for counting the breath interval is updated, and the process will be iterated (referring to FIG. 6).

FIG. 5 is a flow chart showing the low-sensitivity disconnect detection algorithm. As shown, when any of consecutive-breath pressure loss, long-term volume loss and continuous pressure loss is detected in steps 502, 504 and 506, the output of the low-sensitivity circuit disconnect detection is set as logic "1" in step 508, and the main alarm is activated in step 510. When none of the consecutive-breath pressure loss, long-term volume loss and continuous pressure loss has been detected in steps 502, 504 and 506, the output of the low-sensitivity circuit disconnect detection is set as logic "0" in step 512. In one embodiment, the output of the long-term volume loss detection will not be set at logic "1" unless the volume loss has been lasting for minimum periods of time, while the consecutive-pressure loss detection is set at logic "1" only when the breath during which the loss was detected is longer than a minimum period of time or the loss has lasted for two consecutive breaths. Therefore, a volume counter $VOL_{TMR}$ for counting the volume loss time and a breath interval counter $BRTH_{TMR}$ for counting the total breath time are required. In addition, continuous pressure loss is detected whenever such loss is continuous for at least a period of time, thus a continuous pressure loss timer $CONTPRS_{TMR}$ is required for the continuous pressure loss detection.

FIG. 6 shows the complete algorithm of circuit-disconnect detection at both low-sensitivity and high-sensitivity. According to the nature of each detection unit, the consecutive-breath pressure loss detection (step 604), the short-term volume loss detection (steps 606) and the long-term volume loss detection (step 608) normally initiate at the beginning of the inspiratory phase of a breath (step 602). In contrast, the single-breath pressure loss detection (step 616) and compliance change detection (steps 618) typically initiate at the end of the inspiratory phase of the breath (step 614). Therefore, whether the breath taken by the patient is at the beginning of the inspiratory phase is determined in step 602, followed by the consecutive-breath pressure loss detection 604 and the detections of short- and long-term volume loss detections in steps 606 and 608. As the output of consecutive-breath pressure loss is determined based on the peak expiratory pressure $P_{peak}$, the peak expiratory pressure $P_{peak}$ is reset after step 604 at step 610. In addition, the consecutive-breath pressure loss detection requires such loss to be detected when the loss occurs in a breath longer than a minimum period of time or when the loss lasts for two consecutive breaths. Therefore, the breath interval timer $BRTH_{TMR}$ is reset at step 612 after the output of the consecutive-breath pressure loss is obtained in step 604.

When the breath taken by the patient is not at the beginning of the inspiratory phase, whether the breath is at the end of the inspiratory phase is determined in step 614. If, in step 614, it is determined that the patient is at the end of the inspiratory phase, the single-breath pressure loss and the compliance change detections are performed in steps 616 and 618, and the high-sensitivity disconnection output is computed in step 620. The breath interval timer $BRTH_{TMR}$ is then updated in step 622. At any stage of the breath, including the beginning or the end of the inspiratory phase or a stage in between, the continuous pressure loss detection is performed in step 624. This is because the continuous pressure loss is determined based on the expiratory pressure $P_{exp}$ which may vary any time throughout the breath and can be measured any time during the breath, such that the continuous pressure loss is basically independent of breath phase. The peak expiratory pressure $P_{peak}$ is updated in step 626, and the short-term and accumulated inspiratory and expiratory volumes $V_{exp\_brth}$, $V_{insp\_brth}$, $V_{exp}$ and $V_{insp}$ are updated in step 628. The volume timer $VOL_{TMR}$ is updated in step 630, and the low-sensitivity disconnect detection output is computed in step 632. The whole process is re-iterated after step 632.

FIG. 7 shows illustrate the inspiratory gas flow $Q_{insp}$, the expiratory gas flow $Q_{exp}$, the expiratory gas pressure $P_{exp}$, the peak expiratory gas pressure $P_{peak}$, the inspiratory and expiratory gas volume $V_{insp\_brth}$ and $V_{exp\_brth}$ for a single breath, and the accumulated inspiratory and expiratory gas volumes $V_{insp}$ and $V_{exp}$ in response to a circuit disconnect. As shown, in the first two expiratory phases and the first inspiratory phases, the inspiratory flow $Q_{insp}$, the expiratory flow $Q_{exp}$ and the expiratory pressure $P_{exp}$ are similar to those as shown in FIG. 3. When a volume loss or a pressure loss occurs in the second inspiratory phase, the ventilation system automatically elevates inspiratory flow to compensate the loss caused by the circuit disconnect. As shown, the inspiratory flow $Q_{insp}$ is elevated steeply for compensating the loss caused by the circuit disconnect. The elevation of inspiratory flow $Q_{insp}$ is not reset until the patient circuit 20 is reconnected. As disconnect occurs, no expiratory flow can be detected at the expiratory line 24. Therefore, the expiratory flow $Q_{exp}$ remains at zero. The expiratory pressure $P_{exp}$ also falls to a lower value as shown in FIG. 7. As the high-sensitivity disconnect detection is performed for each breath, the output of the high-sensitivity disconnect is typically produced at the end of each inspiratory phase. Depending on the sub-algorithm that detects the low-sensitivity circuit disconnect, the circuit disconnect may be declared at various stages of the breath, so as to activate the main alarm.

Figure 8:
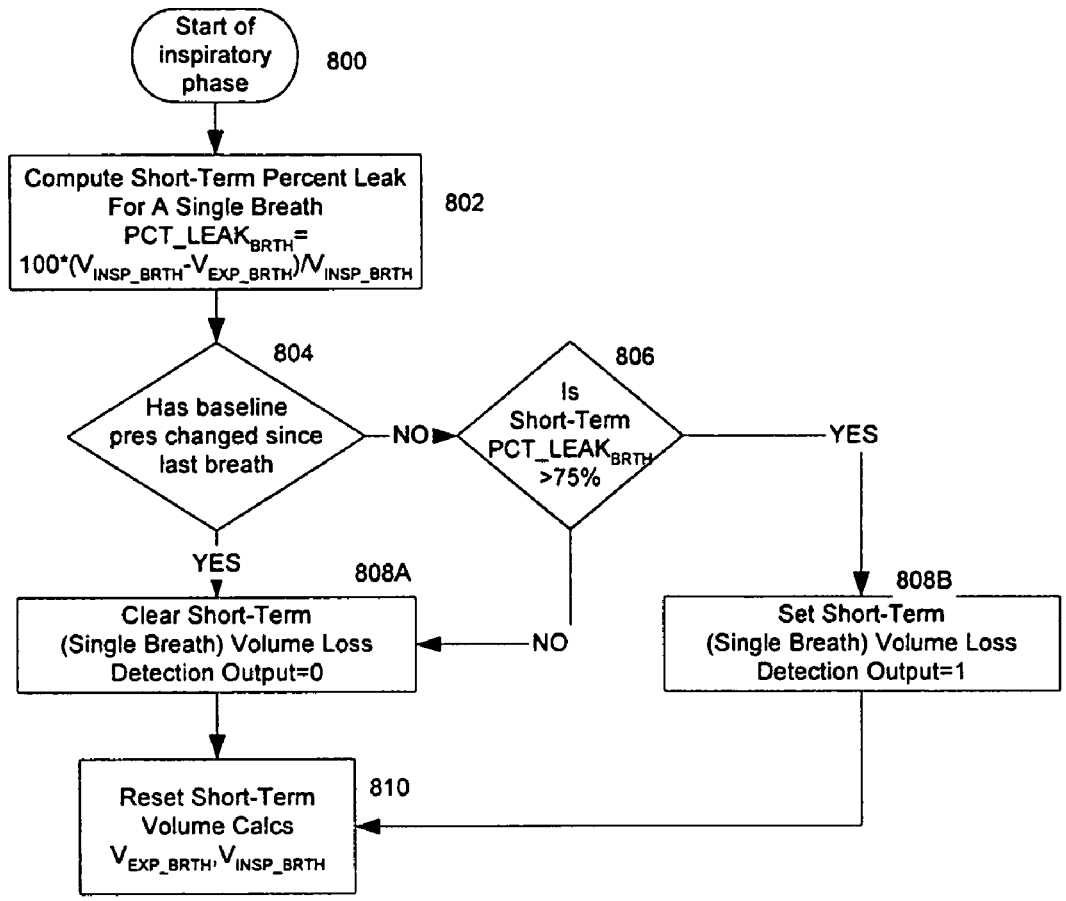
FIG. 8 shows the detailed process flow of the sub-algorithm for detecting a short-term volume loss.
Figure 9:
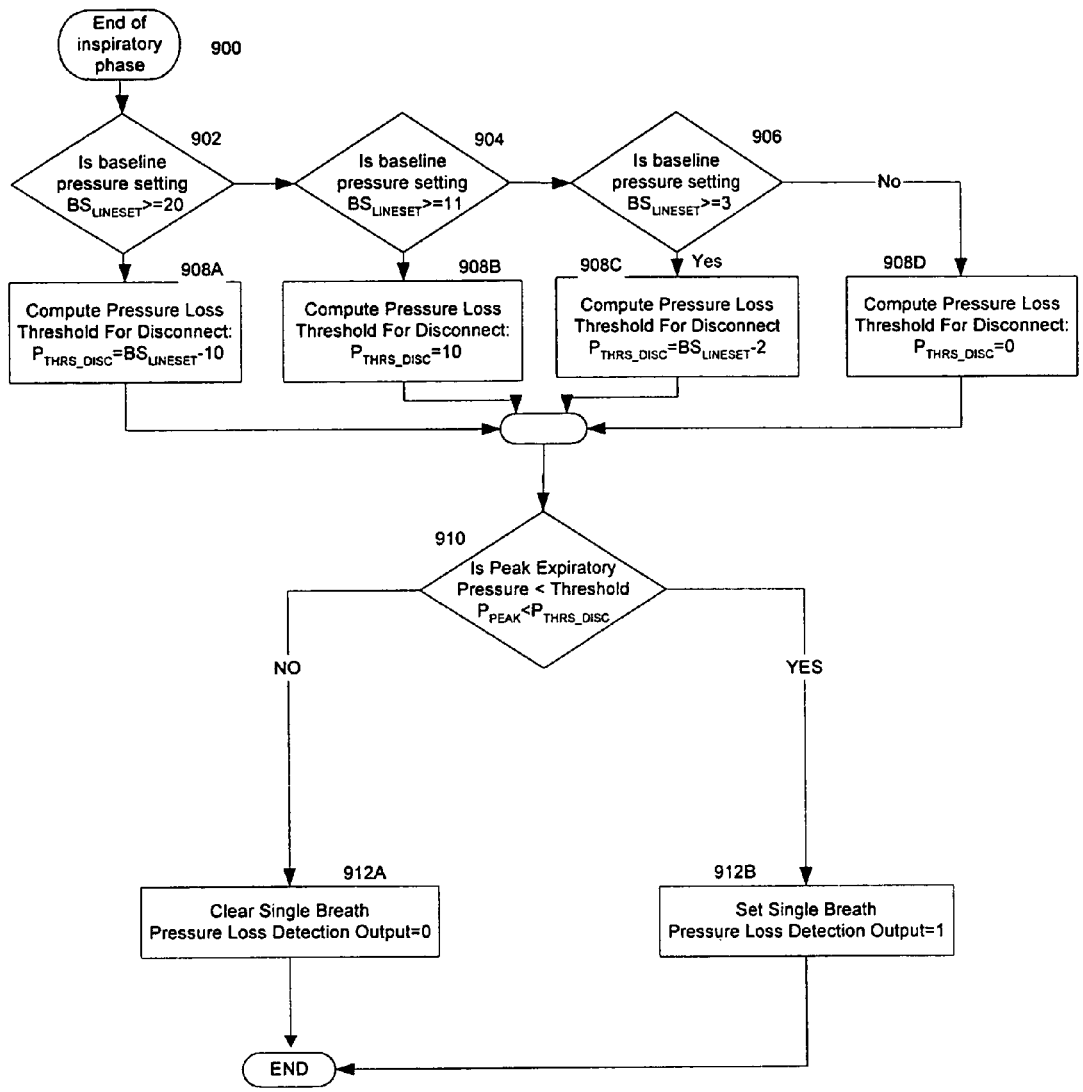
FIG. 9 is a flow chart showing the sub-algorithm for detecting a single-breath pressure loss.
Figure 11:
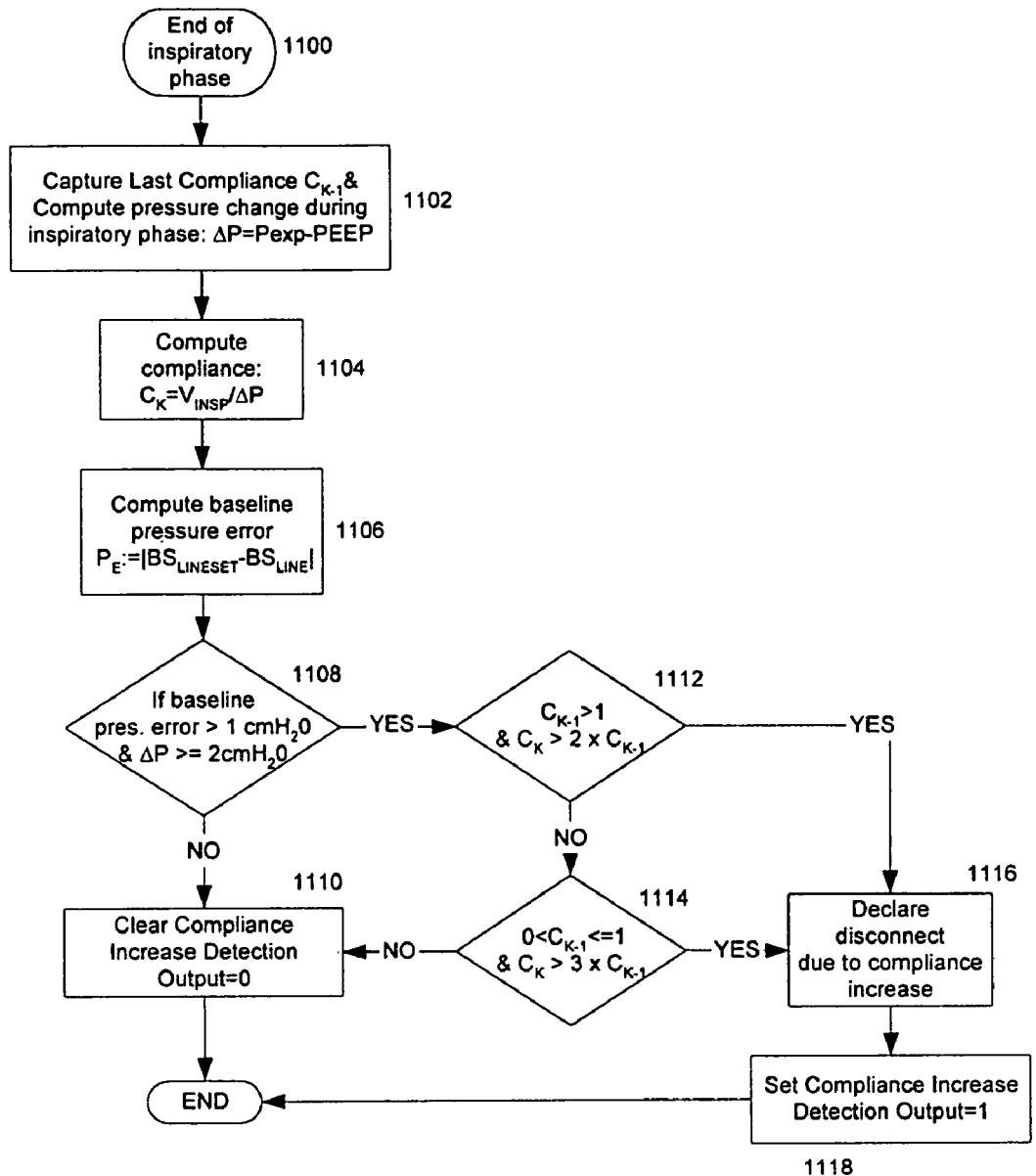
FIG. 11 is a flow chart showing the details of the sub-algorithm for detecting a compliance change caused by circuit disconnect.
Figure 13:
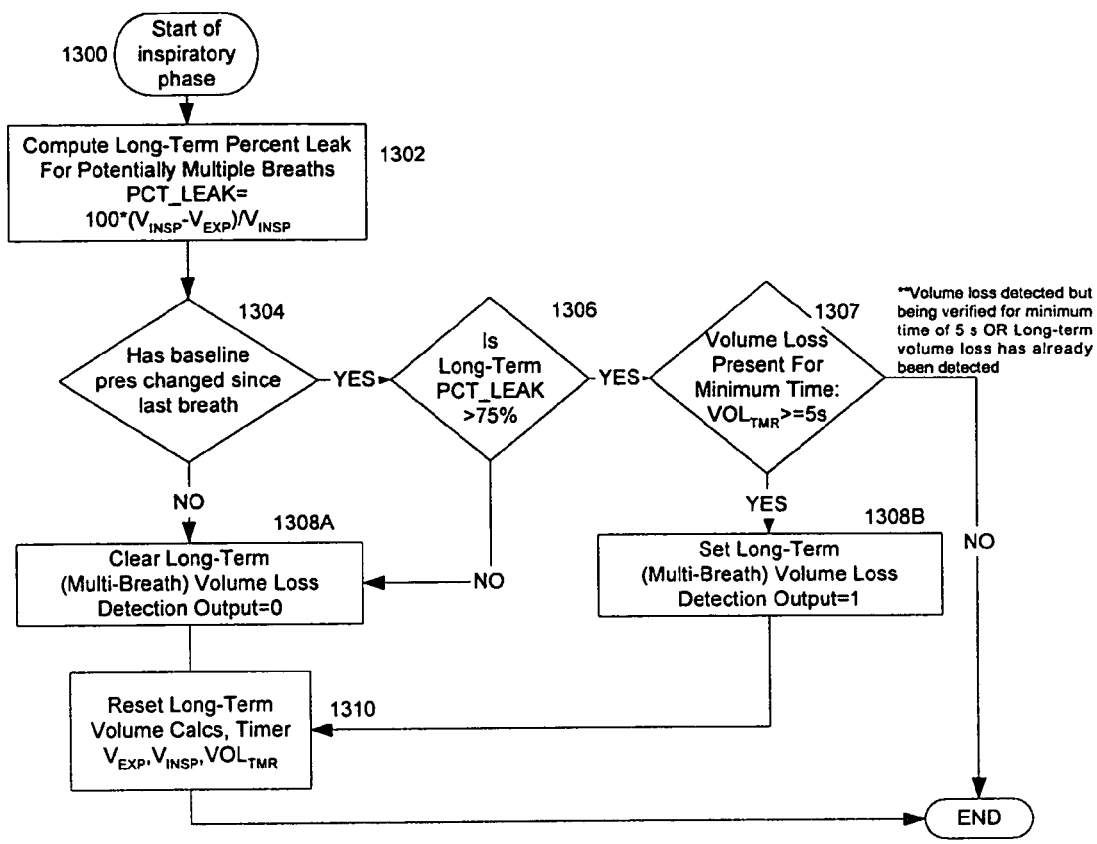
FIG. 13 is a flow chart showing the sub-algorithm for detecting long-term volume loss.
Figure 15:
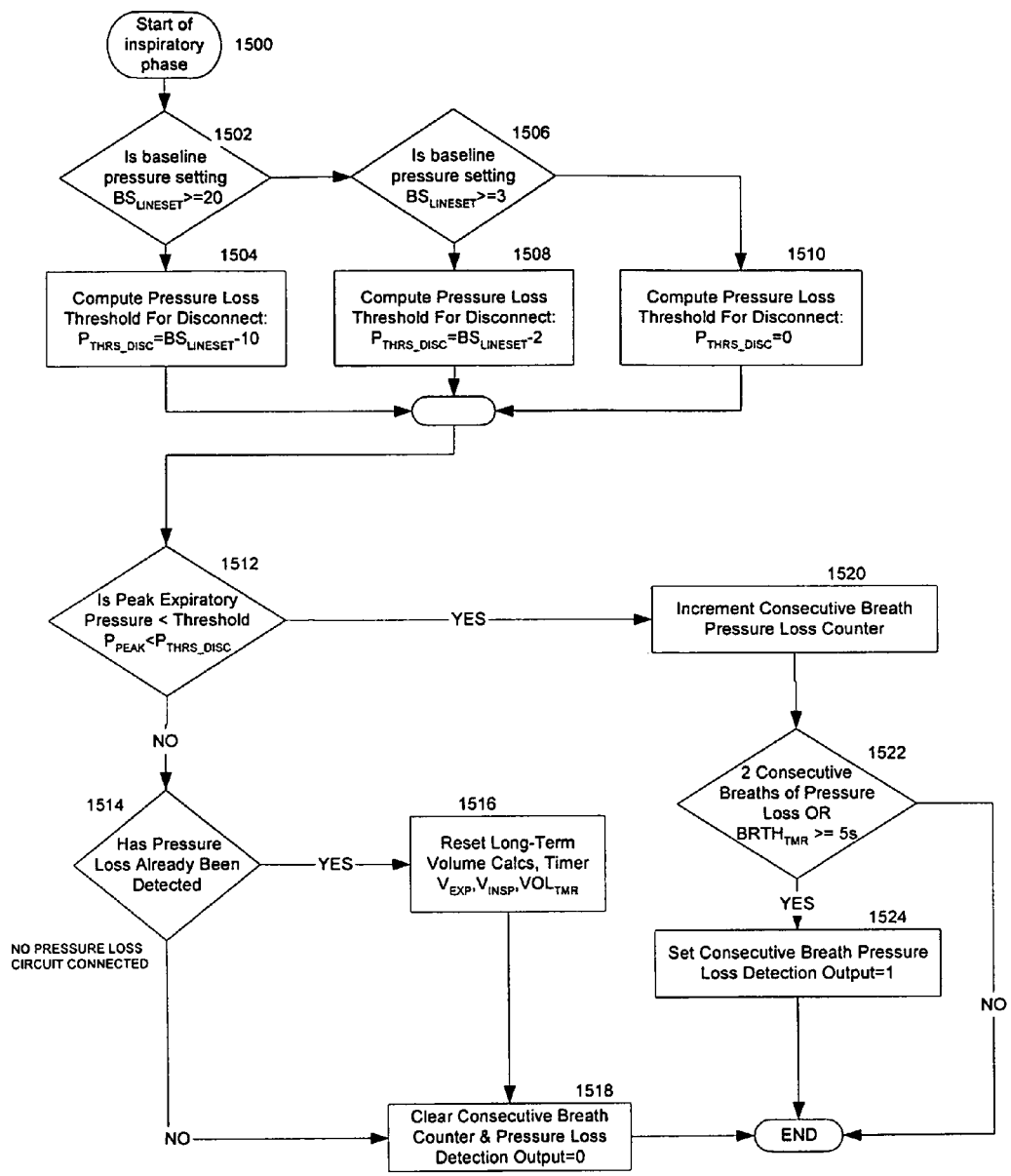
FIG. 15 is a flow chart showing the sub-algorithm for detecting consecutive-breath pressure loss.
Figure 16:
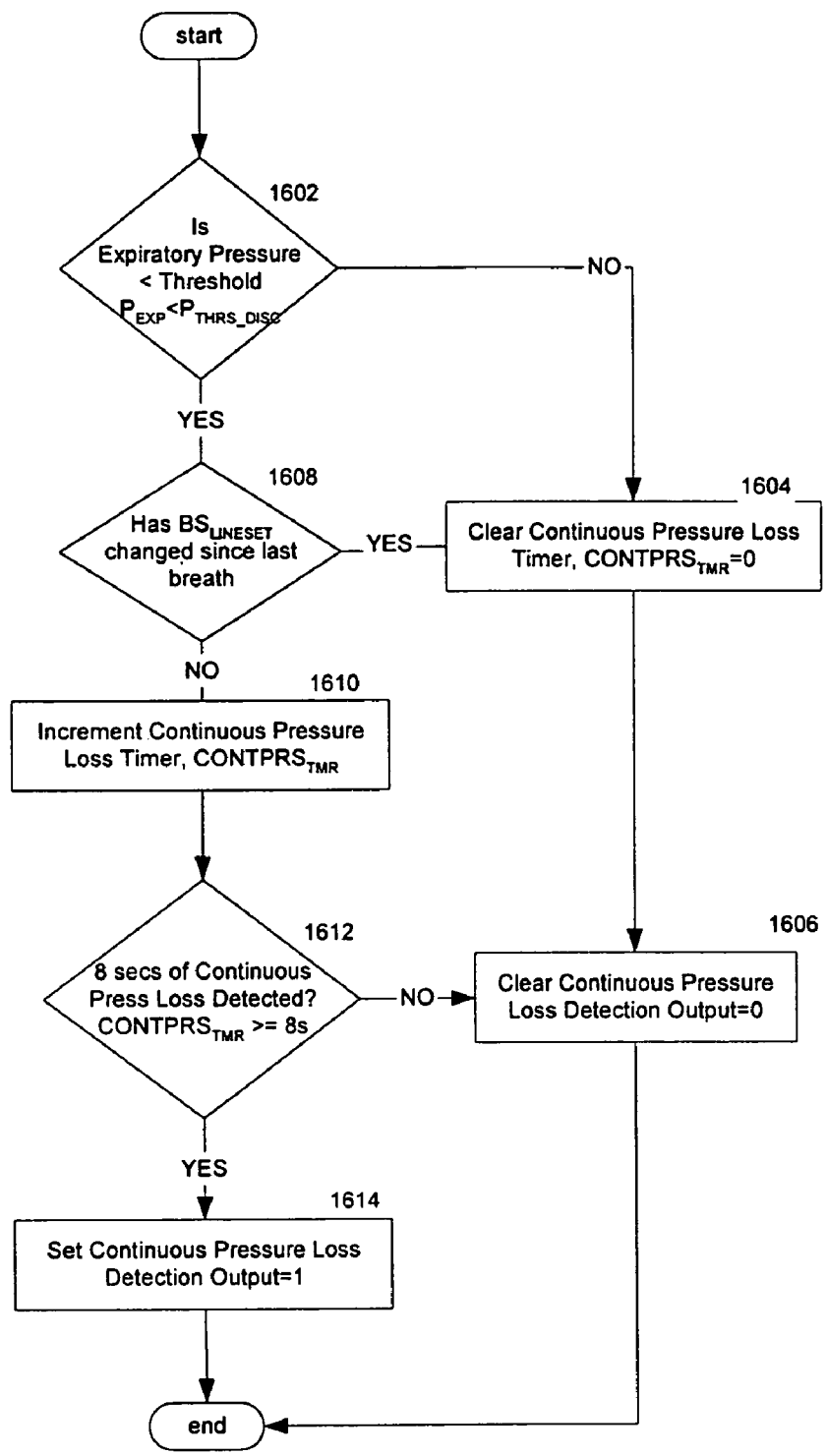
FIG. 16 is a flow chart showing the continuous pressure loss detection algorithm.

FIGS. 8, 9 and 11 illustrates the sub-algorithms for detecting short-term volume loss (step 606), the single-breath pressure loss detection (step 616), and the compliance change (step 618), and FIGS. 13, 15 and 16 illustrate the sub-algorithms for detecting the long-term volume loss detection (step 608), the consecutive-breath pressure loss detection (604) and the continuous pressure loss detection (step 624), respectively. Each of the sub-algorithms will be explained in detail as follows with references to the respective drawing.

As shown in FIG. 8, the short-term volume loss detection initiates at the beginning of the inspiratory phase of each breath in step 800. In step 802, a percentage of volume leakage of the last breath $PCT\_LEAK_{brth}$ can be obtained from equation (1) as:

$$PCT\_LEAK_{brth}=100\times(V_{insp\_brth}-V_{exp\_brth})/V_{insp\_brth} \qquad (1).$$

In one embodiment, the inspiratory gas volume $V_{insp\_brth}$ of the last breath can be obtained by integrating the inspiratory gas flow $Q_{insp}$, and the the expiratory gas volume $V_{exp\_brth}$ of the last breath can be obtained by integrating the expiratory gas flow $Q_{exp}$. In step 804, whether the baseline pressure setting has been changed must be confirmed before detection of volume loss since the change of the baseline pressure setting will cause unbalanced volumes that appear as a volume leakage to ultimately affect the volume loss detection. When a change of the baseline pressure is detected, the short-term volume loss output is set at logic zero in step 808A, and the short-term volume calculation for the inspiratory volume $V_{insp\_brth}$ and the expiratory volume $V_{exp\_brth}$ are reset in step 810. The short-term volume loss detection unit 642 is ready to detect short-term volume loss for the next breath. When the baseline pressure remains unchanged, the percentage of volume leakage is compared to a reference percentage in step 806. The percentage of volume leakage is variable according to various parameters of the ventilation system as well as the physical condition of the patient. In this embodiment, the reference percentage is set at 75%. Therefore, when the percentage of volume leakage is less than or equal to 75%, the process goes to step 808A. The short-term volume loss output is set as 0, and the calculations are reset in step 810. When the percentage of volume leakage is higher than 75%, the short-term volume loss is detected, and the output of the short-term volume loss detection is set at logic 1 in step 808B. After outputting the short-term volume loss detection result, the calculations of the inspiratory and expiratory volumes $V_{insp\_brth}$ and $V_{exp\_brth}$ are reset in step 810, and the short-term volume loss detection unit 642 is ready to detect short-term volume loss for the next breath. Therefore, short-term volume loss detection can also be referred as the single-breath volume loss detection.

FIG. 9 illustrates the process for detecting single-breath pressure loss performed by the single-breath pressure loss detection unit 643. As discussed above, the single-breath pressure loss detection initiates at the end of the inspiratory phase of a breath in step 900. In steps 902 to 908D, a threshold pressure $P_{thrs\_disc}$ is calculated based on a baseline pressure setting $BS_{lineset}$. The threshold pressure $P_{thrs\_disc}$ is used as a reference for determining whether a circuit disconnect occurs due to pressure loss of a single breath. In step 902, the baseline pressure setting $BS_{setline}$ is compared to a first predetermined reference pressure, which is 20 $cmH_2O$ in this embodiment. When the baseline pressure is larger than or equal to 20 $cmH_2O$, a threshold pressure $P_{thrs\_disc}$ is calculated as the baseline pressure minus 10 $cmH_2O$ in step 908A. If the baseline pressure setting $BS_{lineset}$ is smaller than 20 $cmH_2O$, it is further compared to a second reference pressure in step 904, which is 11 cmH$_2$O in this embodiment. When the baseline pressure setting BS$_{lineset}$ is larger than 11 cmH$_2$O, in step 908B, the threshold pressure P$_{thrs\_disc}$ is set at 10 cmH$_2$O. If the baseline pressure setting BS$_{lineset}$ is smaller than 11 cmH$_2$O, it is further compared to a third reference pressure in step 906. In this embodiment, this third reference pressure is 3 cmH$_2$O. Therefore, when the baseline pressure setting BS$_{lineset}$ is equal to or larger than 3 cmH$_2$O, the threshold pressure P$_{thrs\_disc}$ equals to the baseline pressure setting BS$_{lineset}$ minus 2 in step 908C. If not, the threshold pressure P$_{thrs\_disc}$ is set at zero in step 908D. When the threshold pressure P$_{thrs\_disc}$ is determined, in step 910, the peak expiratory pressure P$_{peak}$ is compared to the threshold pressure P$_{thrs\_disc}$. If the peak expiratory pressure P$_{peak}$ is not lower than the threshold pressure P$_{thrs\_disc}$, no pressure loss is detected, that is, the output of single-breath pressure loss detection is set as 0 in step 912A. If the peak expiratory pressure P$_{peak}$ is lower than the threshold pressure P$_{thrs\_disc}$, single-breath pressure loss is detected, and the output for such detection is set as 1 in step 912B.

Referring to FIGS. 3, 7 and 9, the single-breath pressure loss detection typically initiates at the beginning of the inspiratory phase of a breath, while the detection output of the single-breath pressure is normally generated at the beginning of the expiratory phase or the end of the inspiratory phase. For example, as shown in FIG. 7, when a circuit disconnect occurs at the middle of an inspiratory phase, although the expiratory pressure P$_{exp}$ drops lower than the threshold pressure P$_{thrd\_disc}$ immediately, the highest expiratory peak pressure, that is, the peak peak pressure P$_{peak}$ remains higher than the threshold pressure throughout the following expiratory phase. Therefore, no pressure loss can be detected during at the beginning of the inspiratory phase of the following breath. However, as the circuit disconnect has occurred in the previous breath, the expiratory pressure during the following inspiratory phase will remain lower than the threshold pressure P$_{thrd\_disc}$. Therefore, a disconnect can be detected at the beginning of the expiratory phase of the following breath as shown in FIG. 7.

Table I shows the relationship between the threshold pressure P$_{thrs\_disc}$ and the baseline pressure setting BS$_{lineset}$ in this embodiment.

TABLE I

| Baseline Pressure Setting (BS$_{lineset}$) | Pressure Loss Threshold (P$_{thrs\_disc}$) |
|---|---|
| BS$_{lineset}$ 20 cm H$_2$O | BS$_{lineset}$ − 10 |
| 20 cm H$_2$O > (less than only) BS$_{lineset}$ > 11 cm H$_2$O | 10 |
| 11 cm H$_2$O > BS$_{lineset}$ 3 cm H$_2$O | BS$_{lineset}$ − 2 |
| 3 cm H$_2$O > BS$_{lineset}$ | 0 |

It will be appreciated that apart from the relationship as shown in Table I, the relationship can be adjusted according to various parameters of the ventilation system and/or the physical conditions of the patient. For example, Tables II and III show other relationships for determining the threshold pressure P$_{thrs\_disc}$ in accordance with the baseline pressure setting BS$_{lineset}$.

TABLE II

| Baseline Pressure Setting (BS$_{lineset}$) | Pressure Loss Threshold (P$_{thrs\_disc}$) |
|---|---|
| BS$_{lineset}$ 20 cm H$_2$O | BS$_{lineset}$ − 10 |
| 20 cm H$_2$O > BS$_{lineset}$ 3 cm H$_2$O | BS$_{lineset}$ − 2 |
| 3 cm H$_2$O > BS$_{lineset}$ | 0 |

TABLE III

| Baseline Pressure Setting (BS$_{lineset}$) | Pressure Loss Threshold (P$_{thrs\_disc}$) |
|---|---|
| BS$_{lineset}$ 20 cm H$_2$O | BS$_{lineset}$ − 15 |
| 20 cm H$_2$O > BS$_{lineset}$ 9 cm H$_2$O | BS$_{lineset}$ − 5 |
| 9 cm H$_2$O > BS$_{lineset}$ 4 cm H$_2$O | BS$_{lineset}$ − 3.5 |
| 4 cm H$_2$O > BS$_{lineset}$ | 0 |

Figure 10:
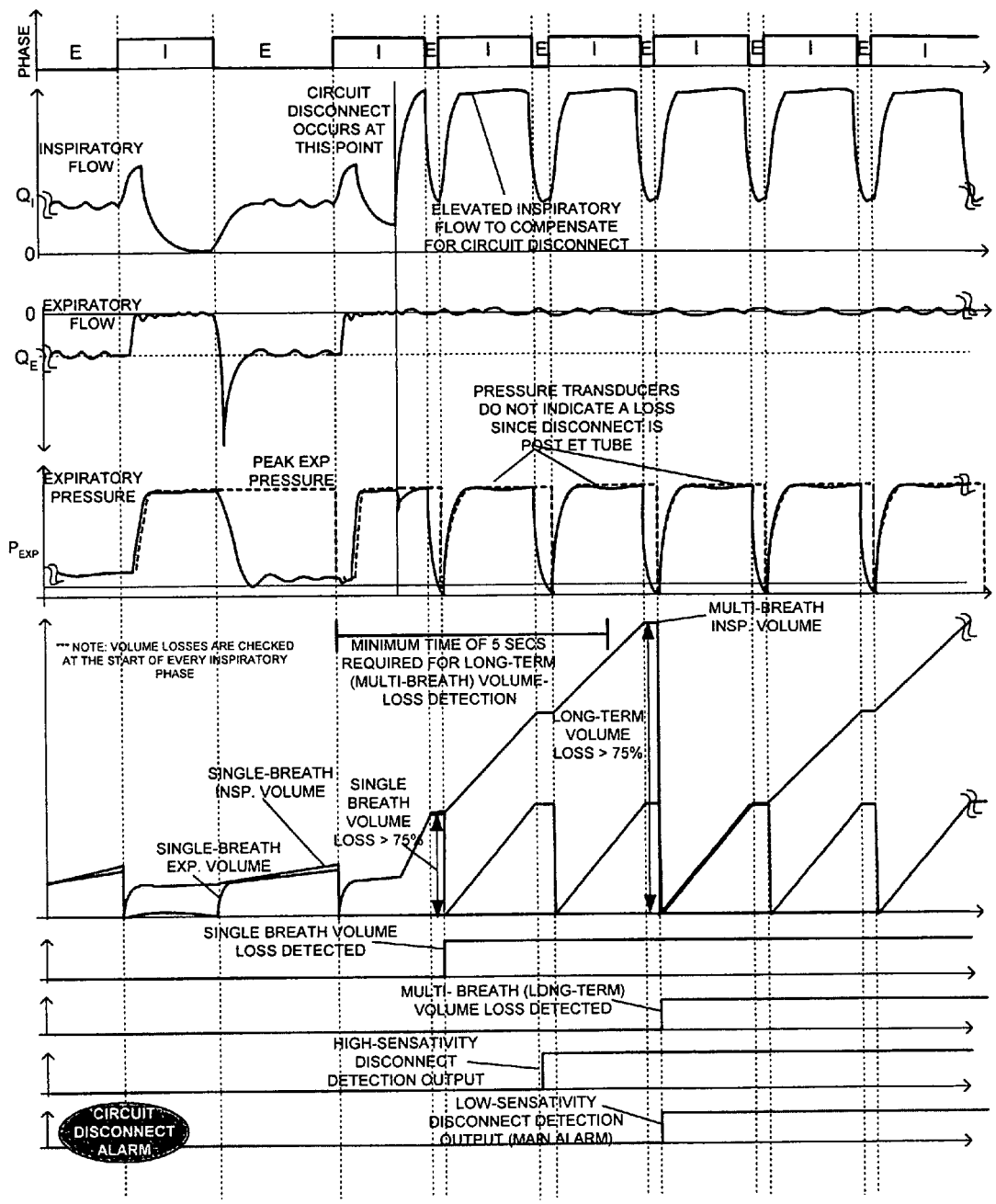
FIG. 10 shows the response of inspiratory and expiratory gas flows and volumes and expiratory pressure when a disconnect occurring at the endotracheal tube.

As mentioned above, the inspiratory and expiratory gas flows Q$_{insp}$ and Q$_{exp}$ are typically measured at the inspiratory and expiratory lines 22 and 24, while the expiratory pressure P$_{exp}$ is typically measured at the Wye fitting 26. The detection based on pressure loss and volume loss thus does not provide direct indication of a circuit disconnect occurring at the endotracheal tube. For example, as shown in FIG. 10, when a circuit disconnect occurs, similar to FIG. 7, the inspiratory gas flow is elevated by the ventilation system to compensate the circuit disconnected. However, the reading of the expiratory pressure does not indicate any loss because the disconnect occurs at the endotracheal tube instead of the Wye fitting 26 and the expiratory line 24. Therefore, in the detection algorithm as provided, compliance change caused by circuit disconnect is detected, such that a more direct indication or information regarding disconnect at the endotracheal tube can be obtained.

FIG. 11 is a flow chart showing the compliance change detection algorithm performed by the compliance change detection unit 641. The compliance C$_k$ is defined as the ratio of the change in volume of inspiratory gas flow ΔV and the pressure change ΔP during an inspiratory phase. In this embodiment, the changing volume of inspiratory gas flow ΔV is equal to the inspiratory gas volume V$_{insp}$ minus zero, which is equal to the inspiratory gas volume V$_{insp}$. It will be appreciated that the changing volume of inspiratory gas flow may vary from the inspiratory gas flow V$_{insp}$ under specific conditions. The pressure change ΔP is the difference between the expiratory pressure P$_{exp}$ measured at the end of the inspiratory phase and the positive end expiratory pressure (PEEP). That is, ΔP=P$_{exp}$−PEEP and C$_k$=V$_{insp}$/ΔP. In this embodiment, the compliance of the previous breath and the current breath is compared to determine whether there is a compliance change due to patient circuit disconnect. As mentioned above, the compliance change detection initiates at the end of the inspiratory phase of a breath in step 1100. In step 1102, the compliance of the previous breath C$_{k-1}$ is captured, and the pressure difference between the expiratory pressure and last PEEP pressure for the inspiratory phase of a current breath is calculated. In step 1104, the compliance of the current breath C$_k$ is calculated. In step 1106, an error P$_E$ of baseline pressure setting is calculated as: P$_E$=|BS$_{lineset}$−BS$_{line}$|. In step 1108, the baseline pressure error P$_E$ and the pressure change during inspiratory phase ΔP are compared with predetermined values, such as 1 cmH$_2$O and 2 cmH$_2$O, respectively. When the pressure error P$_E$ is smaller than 1 cmH$_2$O or the pressure change ΔP is less than 2 cmH$_2$O, the compliance increase detection output is set as 0 in step 1110. When the pressure error P$_E$ is larger than 1 cmH$_2$O and the pressure change ΔP is no smaller than 2 cmH$_2$O, the compliances $C_{k-1}$ and $C_k$ for two consecutive breaths are compared in step 1112. When $C_{k-1}$ is larger than 1 and $C_k$ is larger than $2\times C_{k-1}$, a compliance increase due to disconnect is declared in step 1116, and the compliance increase detection output is set as 1 in step 1118. Also, when $C_{k-1}$ is less than or equal to 1 and larger than 0, and $C_k$ is larger than $3\times C_{k-1}$, the circuit disconnected is declared in step 1116, and the compliance increase detection output is set as 1 in step 1118. If $C_{k-1}$ is no larger than 0 or $C_k$ is no larger than $3\times C_{k-1}$, the compliance increase detection is cleared, and the output of compliance increase detection is set at "0" in step 1110.

Figure 12:
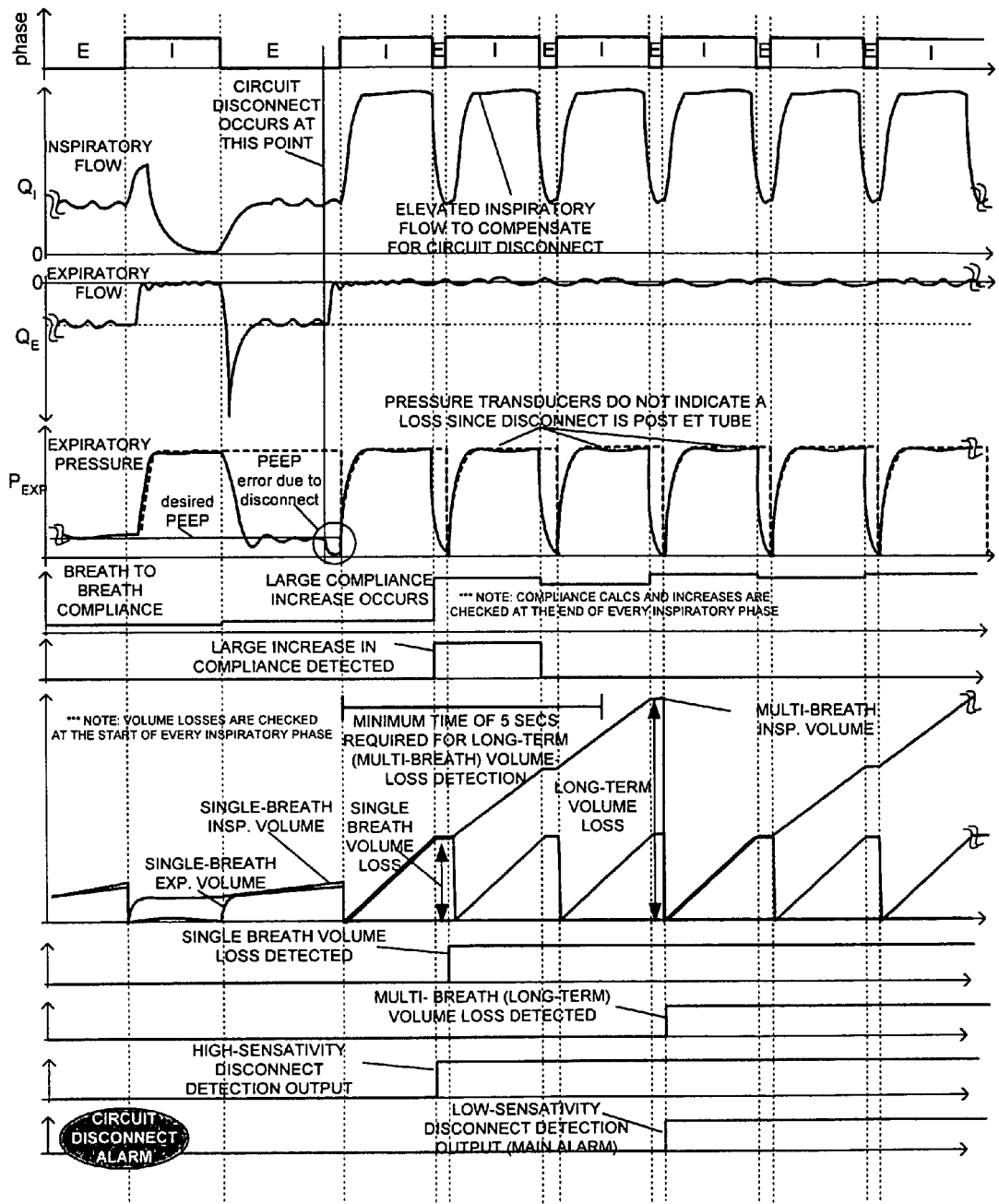
FIG. 12 shows the PEEP error caused by a circuit disconnect occurring at the endotracheal tube.

Referring to FIG. 12, when a circuit disconnect occurs at the endotracheal tube at the end of the expiratory phase, an error of PEEP occurs. The compliance increase is checked at the end of the inspiratory phase for each breath, such the circuit disconnect at the endotracheal tube can be detected.

The detailed procedure of the long-term volume loss detection is illustrated in FIG. 13. Similar to the short-term volume loss detection, the long-term volume loss detection initiates at the beginning of an inspiratory phase in step 1300. In step 1302, the accumulated inspiratory gas volume $V_{insp}$ and the expiratory gas volume $V_{exp}$ obtained by integrating the inspiratory gas flow $Q_{insp}$ and the expiratory gas flow $Q_{exp}$, respectively, are provided to calculate the percentage of volume leakage PCT_LEAK according to equation (1) as previously described. In step 1304, whether the baseline pressure setting has been changed must be confirmed before detection of volume loss since the change of the baseline pressure setting will cause unbalanced volumes that appear as a volume leakage to ultimately affect the volume loss detection. When there is no change of baseline pressure setting, in step 1306, the percentage of volume leakage is compared to a reference percentage, such as 75% in this embodiment. It will be appreciated that such reference percentage may be altered as desired and/or according to the physical conditions of the patient and/or parameters of the ventilation system. When the percentage of volume leakage of the current breath is higher than 75%, whether the computation of the percentage of volume leakage has lasted over a minimum period of time is determined in step 1307. More specifically, the time from the beginning of the inspiratory phase when the long-term volume loss detection initiates is counted by a volume timer or counter $VOL_{TMR}$. The volume timer $VOL_{TMR}$ will not be reset unless the percentage of volume leakage PCT_LEAK drops lower than 75%, since the breathing circuit has been reconnected or due to previous detection of a low-sensitivity circuit disconnect. When the percentage of volume leakage PCT_LEAK over 75% lasts no less than 5 seconds, the long-term volume loss is detected, and the detection output of long-term volume loss is set as "1" in step 1308B. When the leakage percentage $V_{leak\_brth}$ is less than 75% in step 1306, no volume loss is detected, and the volume loss detection output is set at 0 at step 1308A. The calculation of the long-term volume loss, including the volume timer $VOL_{TMR}$, the accumulated expiratory and inspiratory volumes $V_{exp}$ and $V_{insp}$ are reset in step 1310. The long-term volume detection unit 644 is thus ready for detecting the next long-term volume loss, should it occur.

Referring to FIG. 7, when a circuit disconnect occurs to a patient having a breath rate more than 12 BPM, in which each breath is shorter than 5 seconds. As shown, when the percentage of volume leakage is over 75%, the accumulated inspiratory and expiratory gas volumes $V_{insp}$ and $V_{exp}$ are not reset until a long-term volume detection output has been generated although the single-breath inspiratory and expiratory gas volumes $V_{insp\_brth}$ and $V_{exp\_brth}$ are reset for each breath. The volume timer $VOL_{TMR}$ is also continuously updated before the long-term volume loss detection is generated, or the circuit has been reconnected. When the percentage of volume leakage PCT_LEAK over 75% lasts for at least 5 seconds, the long-term volume loss is detected, and the output is set at "1" at the end of the immediately following expiratory phase. Therefore, when each breath taken by the patient is shorter than the minimum period of time defined in the long-term volume loss detection algorithm, the long-term volume loss is normally detected over multiple breaths.

Figure 14:
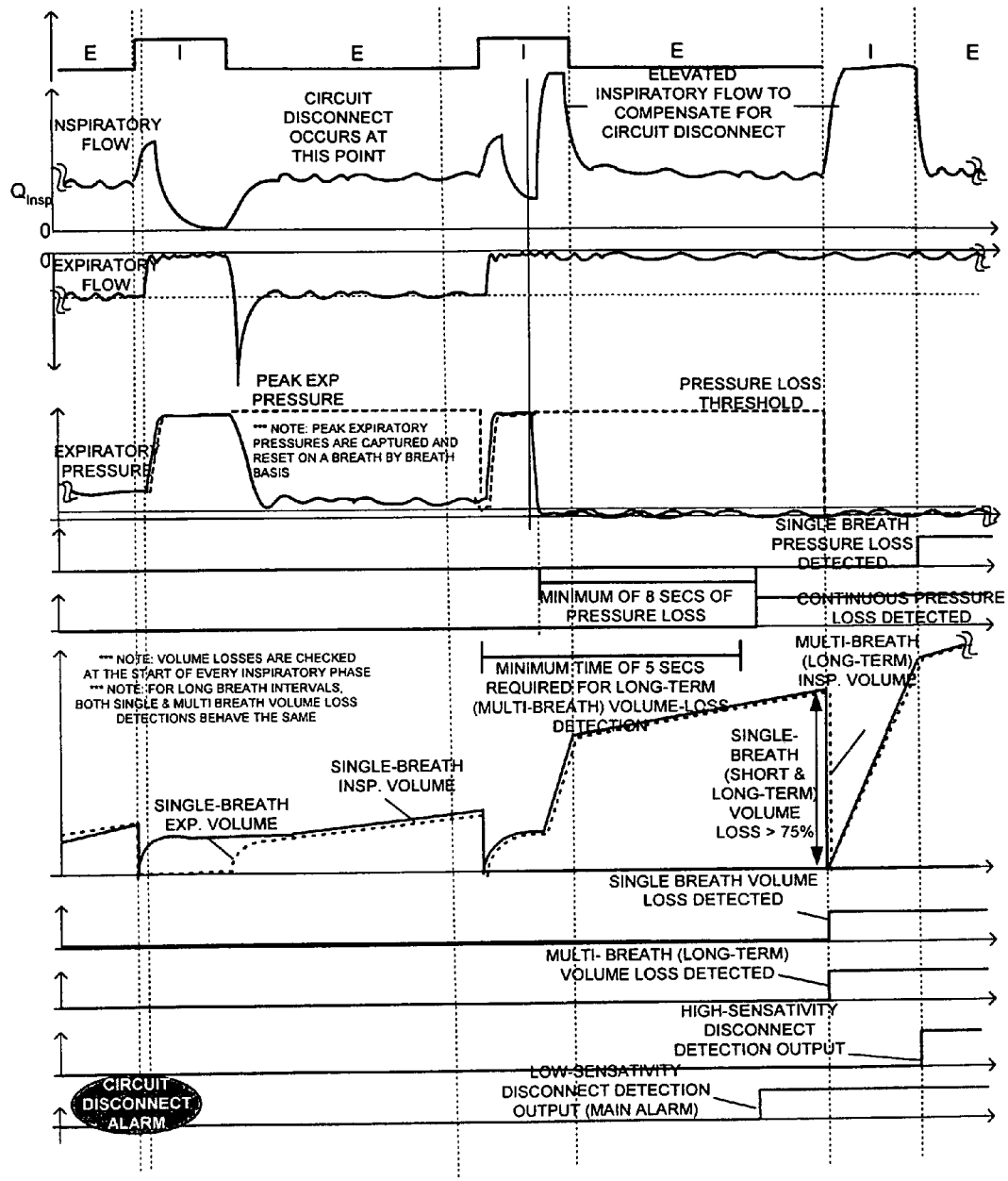
FIG. 14 shows expiratory pressure and inspiratory and expiratory volumes in response to a circuit disconnect with a low breath rate.

FIG. 14 shows a patient having a breath rate less than 12 BPM, in which each breath is longer than 5 seconds. Similarly, the volume timer $VOL_{TMR}$ will not be reset unless a long-term volume loss detection output has been generated or a circuit reconnection has been performed. When the percentage of volume leakage PCT_LEAK over 75% lasts for 5 seconds, with the slow breath rate, the long-term volume loss is detected within a single breath, and the detection output is set at "1" at the end of the current breath. That is, at the end of the expiratory phase of the same breath, or the beginning of the inspiratory phase of the immediately following breath.

FIG. 15 is a flow chart showing the process of the consecutive breath pressure detection algorithm. Similar to the single-breath pressure loss detection algorithm, a pressure loss threshold is set or determined according to a baseline pressure, which, in many ventilation systems, is referred as the positive end expiratory pressure (PEEP). When a peak pressure is lower than the threshold is detected for a breath which lasts over a minimum duration or for two consecutive breaths, the consecutive-breath pressure loss is detected. In step 1500, the consecutive-breath pressure loss algorithm initiates at the beginning of each inspiratory phase. In steps 1502 to 1510, a threshold value for determining the pressure loss caused by circuit disconnect is determined based on the relationship as shown in Table II. Similarly, the threshold pressure can also set up by other relationships such as those shown in Table I and III. In step 1502, if the baseline pressure $BS_{lineset}$ is initially determined to be larger than or equal to a first predetermined value. In this embodiment, the first predetermined value is preferably selected at 20 cmH$_2$O. When the baseline pressure $BS_{lineset}$ is larger than or equal to 20 cmH$_2$O, the pressure loss threshold is computed as $P_{thrs\_disc}=BS_{lineset}-10$ in step 1504. When the baseline pressure $BS_{lineset}$ is less than 20 cmH$_2$O, whether the baseline pressure $BS_{lineset}$ is larger than or equal to a second predetermined value, such as 3 cmH$_2$O is determined in step 1506. If the baseline pressure $BS_{lineset}$ is larger than or equal to 3 cmH$_2$O, the threshold value is calculated by $P_{thrs\_disc}=BS_{lineset}-2$ in step 1508. When the baseline pressure is set less than 3 cmH$_2$O, the threshold value $P_{thrs\_disc}$ is determined equal to zero in step 1510.

When the threshold value $P_{thrs\_disc}$ for determining circuit disconnect is calculated, the peak expiratory pressure $P_{peak}$ is compared to the threshold value $P_{thrs\_disc}$ in step 1512. When the peak expiratory pressure $P_{peak}$ is no smaller than the threshold value $P_{thrs\_disc}$, whether a pressure loss has been detected has to be checked in step 1514. When the disconnect has already been declared and the patient circuit is reconnected, the long-term volume loss calculations, are reset in step 1516 to avoid volume loss disconnect detection upon reconnection. Otherwise, the consecutive-breath pressure loss detection output is set at 0 in step 1518. When the peak pressure $P_{peak}$ falls under the threshold value $P_{thrs\_disc}$ in step 1512 in step 1520, a counter is used to increment the consecutive breath cycles during which the pressure loss detected in step 1512 continues. When the pressure loss detected in step 1512 lasts for more two consecutive breaths, that is, when the breath counter reading is 2, or when the breath interval timer $BRTH_{TMR}$ is over a minimum period of time, which is 5 seconds in this embodiment, the detection output is set at "1" in step 1524 at the end of the expiratory phase when either one of such conditions is satisfied in step 1522. As shown in FIG. 6, the peak expiratory pressure $P_{peak}$ and the breath interval timer $BRTH_{TMR}$ are reset in steps 610 and 612 occurring at the beginning of every inspiratory phase.

FIG. 16 shows the process flow of the continuous pressure loss detection algorithm. The continuous pressure loss detection is particularly applicable when the patient has a breath rate so low, that the circuit disconnect based on two consecutive breaths may endanger the patient. For example, the response of the continuous pressure loss detection algorithm applied to a patient having a breath rate as low as 5 Breaths Per Minute (BPM) is illustrated in FIG. 14. The continuous pressure loss detection algorithm is based on the expiratory pressure $P_{exp}$ and the threshold value of pressure loss $P_{thrs\_disc}$ as defined previously. In step 1602, the expiratory pressure $P_{exp}$ is compared to the threshold pressure $P_{thrs\_disc}$. When the expiratory pressure $P_{exp}$ is higher than the threshold pressure $P_{thrs\_disc}$, a timer for counting the time duration of the continuous pressure loss is zeroed in step 1604, and the continuous pressure loss detection output is set as 0 in step 1606. When the expiratory pressure $P_{exp}$ is again lower than the threshold pressure $P_{thrs\_disc}$, any change in the baseline pressure setting $BS_{lineset}$ is determined. If the baseline pressure setting $BS_{lineset}$ has been changed, the timer is reset to zero in step 1604, and the output of continuous pressure loss detection is set at zero in step 1606. When the baseline pressure setting $BS_{lineset}$ has not been changed, the duration of the pressure loss observed in step 1602 is counted by the timer in step 1610. When the duration exceeds or reaches 8 seconds in step 1612, that is, when the pressure loss continues for at least 8 seconds, the continuous pressure loss detection output is set at 1 in step 1614. Otherwise, the continuous pressure loss detection output is set at 0 in step 1606.

The threshold value of the continuous pressure loss can also be varied from that defined in the consecutive-breath pressure loss detection algorithm. For example, as shown in Table III, the threshold pressure $P_{thrs\_disc}$ can also be set as 15, $BS_{lineset}$–5, $BS_{lineset}$–3.5 and 0 when the baseline pressure is no less than 20 cmH$_2$O, less than 20 cmH$_2$O and no less than 9 cmH$_2$O, less than 9 cmH$_2$O and no less than 4 cmH$_2$O, and less than 4 cmH$_2$O, respectively. In addition, as the expiratory pressure varies at any time or any stage when a disconnect occurs, the continuous pressure loss detection does not depend on the phase of the breath. In other words, the detection output may be generated any time regardless the phase of the breath. For example, as shown in FIG. 14, the continuous pressure loss detected for 8 seconds generates an alarm output during an expiratory phase.

The above description is given by way of example, and not limitation. Given the above disclosure, one skilled in the art could devise variations that are within the scope and spirit of the invention. Further, the various features of this invention can be used along, or in varying combinations with each other and are not intended to be limited to the specific combination described herein. Thus, the invention is not to be limited by the illustrated embodiments but is to be defined by the following claims when read in the broadest reasonable manner to preserve the validity of the claims.

What is claimed is:

1. A system for detecting disconnect of a patient circuit of a ventilation system, comprising:
    a) means for detecting a volume loss lasting for a first predetermined period of time;
    b) means for detecting a pressure loss lasting for at least two consecutive breaths or for a breath longer than a second predetermined period of time;
    c) means for detecting a pressure loss continuing for a third predetermined period of time;
    d) means for detecting a volume loss for a single breath;
    e) means for detecting a pressure loss for a single breath; and
    f) means for detecting an increase of compliance,
    wherein the detecting for a)-c) result in generating an alarm, during an inhalation phase and wherein the detecting for d)-f) result in a signal, during an inhalation phase, for adjusting operations instead of the generating of the alarm.

2. The system of claim 1, further comprising means for activating the alarm when the circuit disconnect is detected in any of steps (a), (b) and (c).

3. The system of claim 1, further comprising means for informing subsystems of the ventilation system of the circuit disconnect is detected in step (d), (e) or (f).

4. The system of claim 1, wherein the first predetermined period of time is 5 seconds.

5. The system of claim 1, wherein the second predetermined period of time is 5 seconds.

6. The system of claim 1, wherein the third predetermined period of time is 8 seconds.

7. The system of claim 1, wherein (a) comprises:
    a1) calculating a first volume leakage percentage for a breath;
    a2) comparing the volume leakage percentage to a reference percentage only when a baseline pressure setting is unchanged; and
    a3) setting a detection output as logic 1 when the volume leakage percentage larger than the reference percentage lasts for the first predetermined period of time.

8. The system of claim 7, further comprising:
    a4) setting a detection output as logic 0 when the volume leakage percentage is smaller than the reference percentage or the baseline pressure setting has been changed.

9. The system of claim 8, further comprising:
    a5) resetting calculation of the percentage of volume leakage after steps (a3) or (a4).

10. The system of claim 7, wherein the reference percentage is 75%.

11. The system of claim 7, wherein the volume percentage leakage is calculated by a ratio of a difference between inspiratory and expiratory gas volumes and the inspiratory gas volume of each breath.

12. The system of claim 11, wherein the inspiratory and expiratory gas volumes are obtained by integrating inspiratory and expiratory flow rates, respectively.

13. The system of claim 1, wherein (a) initiates at the beginning of the inspiratory phase of the breath.

14. The system of claim 1, wherein (b) initiates at the beginning of the inspiratory phase of the breath.

15. The system of claim 1, wherein (b) comprises:
    b1) means for determining a threshold pressure according to a baseline pressure setting;
    b2) means for comparing a peak expiratory pressure to the threshold pressure;
    b3) means for incrementing a consecutive breath pressure loss counter when the peak expiratory pressure is smaller than the threshold pressure;
    b4) means for counting a time interval of a breath during which the peak expiratory pressure is smaller than the threshold pressure; and b5) means for setting a consecutive breath pressure loss detection output as logic 1 when the increment of the consecutive breath pressure loss is at least 2 or the time interval is no shorter than the second predetermined period of time.

16. The system of claim 15, wherein b1) further comprises:
means for setting the threshold pressure as the baseline pressure setting minus 10 cmH20 when the baseline pressure is equal to or larger than 20 cmH20;
means for setting the threshold pressure as the baseline pressure setting minus 2 cmH20 when the baseline pressure setting is no less than 3 cmH20; and
means for setting the threshold pressure as 0 when the baseline pressure setting is less than 3 cmH20.

17. The system of claim 15, further comprising means for resetting a long-term volume calculation and a volume timer when the peak expiratory pressure is greater than the threshold pressure and when a pressure loss has been detected already.

18. The system of claim 17, further comprising means for setting the consecutive breath pressure loss detection as logic 0 when the long-term volume calculation and timer have been reset.

19. The system of claim 17, further comprising means for setting the consecutive breath pressure loss detection as logic 0 when the peak expiratory pressure is greater than the threshold pressure and no pressure loss has been detected.

20. The system of claim 1, wherein (c) comprises:
c1) means for comparing an expiratory pressure to a threshold pressure determined based on a baseline pressure setting;
c2) means for counting the time that the expiratory pressure being continuously smaller than the threshold pressure when the baseline pressure has not been changed since last breath; and
c3) means for setting a continuous pressure loss detection output as logic 1 when the time is no shorter than 8 seconds.

21. The system of claim 20, further comprising means for setting the continuous pressure loss detection output as logic 0 when the expiratory pressure is larger than the threshold pressure setting and/or the baseline pressure setting has been changed since the last breath.

22. The system of claim 1, wherein (d) comprises:
d1) means for calculating a volume leakage percentage for a breath;
d2) means for comparing the volume leakage percentage to a reference percentage only when a baseline pressure setting is unchanged; and
d3) means for setting a short-term volume loss detection output as logic 1 when the volume leakage percentage is larger than the reference percentage.

23. The system of claim 22, wherein (d) further comprises:
d4) means for resetting calculation of volumes of inspiratory and expiratory gases for a next breathing cycle.

24. The system of claim 22, wherein the reference percentage is 75%.

25. The system of claim 22, wherein the volume percentage leakage is calculated by a ratio of a difference between inspiratory and expiratory gas volumes and the inspiratory volume of each breathing cycle.

26. The system of claim 25, wherein the inspiratory and expiratory gas volumes are obtained by integrating inspiratory and expiratory flow rates, respectively.

27. The system of claim 22, further comprising means for setting the short-term volume loss detection output as logic 0 when the baseline pressure setting has changed and/or the first volume leakage percentage is less than the reference percentage.

28. The system of claim 1, wherein (d) initiates at the beginning of the inspiratory phase of each breath.

29. The system of claim 1, wherein (e) comprises:
e1) means for comparing a peak expiratory pressure to a threshold pressure determined according to a baseline pressure setting;
e2) means for setting a single-breath pressure loss detection output as logic 0 when the expiratory peak pressure is no less than the threshold pressure; and
e3) means for setting the single-breath pressure loss detection output as logic 1 when the expiratory peak pressure is smaller than the threshold pressure.

30. The system of claim 1, wherein (e) comprises means for detecting a pressure loss for a single breath starts at the end of an inspiratory phase of a breathing cycle for the single breath.

31. The system of claim 1, wherein (f) comprises:
f1) means for computing a pressure difference between an expiratory pressure and a positive expiratory end pressure;
f2) means for computing a compliance for a first and a second inspiratory phases for two consecutive breathing cycles;
f3) means for computing a baseline pressure error;
f4) means for comparing the baseline pressure error with a predetermined error and the pressure difference with a reference error;
f5) means for comparing the compliance for the first and second inspiratory phases; and
f6) means for declaring a disconnect by compliance increase when:
i) the baseline pressure error is larger than the predetermined error;
ii) the pressure difference is no less than the reference error;
iii) the compliance for the first inspiratory phase is larger than a first predetermined compliance value; and
iv) the compliance for the second inspiratory phase is larger than 2 times the compliance for the first inspiratory phase.

32. The system of claim 31, wherein the predetermined error is 1 cmH20.

33. The system of claim 31, wherein the reference error is 2 cmH20.

34. The system of claim 31, wherein the first predetermined compliance value is 1 ml/cmH20.

35. The system of claim 31, further comprising means for setting a compliance increase detection output as 1 when the disconnect caused by the compliance increase is declared.

36. The system of claim 31, further comprising means for declaring a disconnect caused by compliance increase when:
the compliance for the first inspiratory phase is no greater than the first predetermined compliance value and larger than a second predetermined compliance value; and
the compliance for the second inspiratory phase is larger than 3 times the compliance for the first inspiratory phase.

37. The system of claim 36, wherein the first predetermined compliance value is 1 and the second predetermined compliance value is o.

38. A ventilation system, comprising:
an inspiratory flow sensor operative to measure an inspiratory flow of a patient
circuit of the ventilation system;

an expiratory flow sensor operative to measure an expiratory flow of the patient circuit;
a pressure sensor operative to measure an expiratory pressure of the patient circuit;
a first set of processing units comprising:
   a long-term volume loss detection unit, operative to detect volume loss lasting for at least a first predetermined period of time;
   a consecutive pressure loss detection unit, operative to detect pressure loss lasting for at least two consecutive breathing cycles or a second predetermined period of time; and
   a continuous pressure loss detection unit, operative to detect pressure loss continuing for at least a third predetermined period of time; and
a second set of processing units comprising:
   a short-term volume loss detection unit, operative to detect volume loss for a single breathing cycle;
   a single-breath pressure loss detection unit, operative to detect pressure loss for a single breathing cycle; and
   a compliance increase detection unit, operative to detect compliance increase caused by circuit disconnect,
   wherein any one or more of the detecting operations associated with the first set of processing units result in generating an alarm, during an inhalation phase,
   wherein any one or more of the detecting operations associated with the second set of processing units result in a signal, during an inhalation phase, for adjusting operations of the ventilation system instead of the generating of the alarm.

39. The system of claim 38, further comprising the alarm activated whenever any of the first set of processing units detects a circuit disconnect.

40. The system of claim 38, wherein the second set of processing units is operative to inform subsystems of the ventilation system of a circuit disconnect detected thereby.

41. The system of claim 38, wherein the first set of processing units detect a circuit disconnect less sensitive than the second set of processing units.

42. A device for detecting a disconnect occurring to a patient circuit of a ventilation system, comprising:
   a first processor for generating a primary output to a main alarm and detecting a circuit disconnect of the patient circuit through signal transmitted from a flow sensor and a pressure sensor; and
   a second processor for generating a secondary output to inform onboard subsystems of the ventilation system and detecting a circuit disconnect of the patient circuit through signal transmitted from the flow sensor and the pressure sensor,
   wherein the detection of the patient circuit disconnect of the first processor is less sensitive than that of the second processor,
   wherein each processor generates its respective output during an inspiratory phase of a patient breathing cycle, and
   wherein the first processor generates the alarm during the inspiratory phase and the second processor generates a signal, during the inspiratory phase, for adjusting learning operations instead of the alarm.

43. The device of claim 42, wherein the first processor comprises:
   a first processing unit operative to detect a volume loss lasting for a first minimum period of time;
   a second processing unit operative to detect a pressure loss of peak expiratory pressure lasting for at least a second minimum period of time or two consecutive breaths; and
   a third processing unit operative to detect a continuous pressure loss lasting for a third minimum period of time.

44. The device of claim 42, wherein the second processor comprises:
   a first processing unit operative to detect a volume loss occurring within a single breath;
   a second processing unit operative to detect a pressure loss of peak expiratory pressure for a single breath; and
   a third processing unit operative to a compliance increase caused by circuit disconnect.

* * * * *